US009889299B2

(12) United States Patent
Ni et al.

(10) Patent No.: US 9,889,299 B2
(45) Date of Patent: Feb. 13, 2018

(54) TRANSVENOUS METHOD OF TREATING SLEEP APNEA

(75) Inventors: Quan Ni, Shoreview, MN (US); Mark A. Christopherson, Shoreview, MN (US); Timothy P. Herbert, Maple Grove, MN (US); John Rondoni, Plymouth, MN (US)

(73) Assignee: Inspire Medical Systems, Inc., Maple Grove, MN (US)

( * ) Notice: Subject to any disclaimer, the term of this patent is extended or adjusted under 35 U.S.C. 154(b) by 1720 days.

(21) Appl. No.: 13/121,862

(22) PCT Filed: Sep. 30, 2009

(86) PCT No.: PCT/US2009/059060
§ 371 (c)(1),
(2), (4) Date: Apr. 29, 2011

(87) PCT Pub. No.: WO2010/039853
PCT Pub. Date: Apr. 8, 2010

(65) Prior Publication Data
US 2011/0202119 A1 Aug. 18, 2011

Related U.S. Application Data

(60) Provisional application No. 61/101,952, filed on Oct. 1, 2008.

(51) Int. Cl.
*A61N 1/36* (2006.01)
*A61B 5/00* (2006.01)
(Continued)

(52) U.S. Cl.
CPC .......... *A61N 1/3601* (2013.01); *A61B 5/4818* (2013.01); *A61F 2/848* (2013.01); *A61F 2/86* (2013.01); *A61N 1/37205* (2013.01)

(58) Field of Classification Search
CPC .. A61N 1/3611; A61N 1/3601; A61N 1/3605; A61N 1/36057; A61B 5/4818; A61B 5/0031; A61F 5/56
(Continued)

(56) References Cited

U.S. PATENT DOCUMENTS 4,154,247 A    5/1979   O'Neill
4,379,462 A    4/1983   Borkan
(Continued)

FOREIGN PATENT DOCUMENTS

DE    10103288       8/2002
JP    2004529707     9/2004
(Continued)

OTHER PUBLICATIONS

Eisele Article—David W. Eisele, MD et al., "Tongue neuromuscular and direct hypoglossal nerve stimulation for obstructive sleep apnea," Otolaryngologic Clinics of North America, Otolayngol Clin N Am 36 (2003) 501-510 (10 pages).
Goodall Article—Eleanor V. Goodhall et al., "Position-Selective Activation of Peripheral Nerve Fibers with a Cuff Electrode," IEEE Transaction on Biomedical Engineering, vol. 43, No. 8, Aug. 1996, pp. 851-856.
(Continued)

*Primary Examiner* — Amanda Patton
(74) *Attorney, Agent, or Firm* — Dicke, Billig, & Czaja, PLLC

(57) ABSTRACT
A system and method for treating sleep apnea includes inserting an implantable pulse generator subcutaneously within a body of a patient and connecting a lead to the pulse generator. The lead is inserted within the vasculature and advanced transvenously through the vasculature until a stimulation portion of the lead becomes positioned in close proximity to the hypoglossal nerve. A nerve-stimulation signal is applied to the hypoglossal nerve via the stimulation portion of the lead.

30 Claims, 13 Drawing Sheets

(51) Int. Cl.
  *A61F 2/848* (2013.01)
  *A61F 2/86* (2013.01)
  *A61N 1/372* (2006.01)

(58) Field of Classification Search
  USPC .......................................................... 607/42
  See application file for complete search history.

(56) References Cited

U.S. PATENT DOCUMENTS

| | | | |
|---|---|---|---|
| 4,414,986 A | 11/1983 | Dickhudt et al. | |
| 4,567,892 A | 2/1986 | Plicchi et al. | |
| 4,573,481 A | 3/1986 | Bullara | |
| 4,630,614 A | 12/1986 | Atlas | |
| 4,830,008 A | 5/1989 | Meer | |
| 4,960,133 A | 10/1990 | Hewson | |
| 4,967,755 A | 11/1990 | Pohndorf | |
| 5,016,808 A | 5/1991 | Heil, Jr. et al. | |
| 5,105,826 A | 4/1992 | Smits et al. | |
| 5,121,754 A | 6/1992 | Mullett | |
| 5,158,080 A | 10/1992 | Kallok | |
| 5,178,156 A | 1/1993 | Takishima et al. | |
| 5,226,427 A | 7/1993 | Buckberg | |
| 5,230,338 A | 7/1993 | Allen | |
| 5,238,006 A | 8/1993 | Markowitz | |
| 5,265,624 A | 11/1993 | Bowman | |
| 5,281,219 A | 1/1994 | Kallok | |
| 5,282,468 A | 2/1994 | Klepinski | |
| 5,344,438 A | 9/1994 | Testerman | |
| 5,351,394 A | 10/1994 | Weinberg | |
| 5,354,318 A * | 10/1994 | Taepke ............... A61N 1/36528 | 600/368 |
| 5,388,578 A | 2/1995 | Yomtov et al. | |
| 5,522,862 A * | 6/1996 | Testerman et al. ............. 607/42 | |
| 5,531,778 A | 7/1996 | Mashino et al. | |
| 5,540,731 A | 7/1996 | Testerman | |
| 5,540,732 A * | 7/1996 | Testerman ...................... 607/42 | |
| 5,540,733 A * | 7/1996 | Testerman et al. ............. 607/42 | |
| 5,540,734 A | 7/1996 | Zabara | |
| 5,549,655 A * | 8/1996 | Erickson ............. A61N 1/3601 | 607/42 |
| 5,560,372 A | 10/1996 | Cory | |
| 5,591,216 A | 1/1997 | Testerman et al. | |
| 5,843,135 A | 12/1998 | Weijand et al. | |
| 6,006,134 A | 12/1999 | Hill et al. | |
| 6,015,389 A | 1/2000 | Brown | |
| 6,025,624 A | 2/2000 | Figura | |
| 6,041,780 A | 3/2000 | Richard et al. | |
| 6,051,017 A | 4/2000 | Loeb et al. | |
| 6,052,624 A | 4/2000 | Mann | |
| 6,125,290 A | 9/2000 | Miesel | |
| 6,134,459 A | 10/2000 | Roberts et al. | |
| 6,144,866 A | 11/2000 | Miesel et al. | |
| 6,172,772 B1 | 1/2001 | Steinle et al. | |
| 6,175,767 B1 | 1/2001 | Doyle | |
| 6,181,961 B1 | 1/2001 | Prass | |
| 6,198,952 B1 | 3/2001 | Miesel | |
| 6,240,316 B1 | 5/2001 | Richmond et al. | |
| 6,251,126 B1 | 6/2001 | Ottenhoff et al. | |
| 6,269,269 B1 * | 7/2001 | Ottenhoff et al. ............. 607/42 | |
| 6,345,202 B2 | 2/2002 | Richmond et al. | |
| 6,361,494 B1 | 3/2002 | Llndenthaler | |
| 6,366,815 B1 | 4/2002 | Haugland et al. | |
| 6,393,325 B1 | 5/2002 | Mann | |
| 6,445,953 B1 * | 9/2002 | Bulkes et al. .................. 607/33 | |
| 6,449,507 B1 | 9/2002 | Hill et al. | |
| 6,456,866 B1 | 9/2002 | Durand et al. | |
| 6,511,458 B2 | 1/2003 | Milo et al. | |
| 6,532,388 B1 | 3/2003 | Hill et al. | |
| 6,535,759 B1 | 3/2003 | Epstein et al. | |
| 6,542,776 B1 | 4/2003 | Gordon et al. | |
| 6,572,543 B1 * | 6/2003 | Christopherson et al. ... 600/300 | |
| 6,587,725 B1 | 7/2003 | Durand et al. | |
| 6,606,521 B2 | 8/2003 | Paspa et al. | |
| 6,609,032 B1 | 8/2003 | Woods et al. | |
| 6,645,143 B2 | 11/2003 | Van Tassel et al. | |
| 6,647,289 B2 | 11/2003 | Prutchi | |
| 6,651,652 B1 | 11/2003 | Ward | |
| 6,654,634 B1 | 11/2003 | Prass | |
| 6,718,208 B2 | 4/2004 | Hill et al. | |
| 6,731,976 B2 | 5/2004 | Penn et al. | |
| 6,735,471 B2 | 5/2004 | Hill et al. | |
| 6,752,765 B1 | 6/2004 | Jensen et al. | |
| 6,770,022 B2 | 8/2004 | Mechlenburg et al. | |
| 6,805,667 B2 | 10/2004 | Christopherson et al. | |
| 6,829,508 B2 | 12/2004 | Schulman et al. | |
| RE38,705 E | 2/2005 | Hill et al. | |
| 6,881,192 B1 | 4/2005 | Park | |
| 6,893,405 B2 | 5/2005 | Kumar et al. | |
| 6,904,320 B2 | 6/2005 | Park et al. | |
| 6,907,293 B2 | 6/2005 | Grill | |
| 6,928,324 B2 * | 8/2005 | Park et al. ...................... 607/20 | |
| 6,936,011 B2 | 8/2005 | Sheldon | |
| 6,978,171 B2 | 12/2005 | Goetz et al. | |
| 6,999,819 B2 | 2/2006 | Swoyer et al. | |
| 7,054,692 B1 | 5/2006 | Whitehurst et al. | |
| 7,077,810 B2 | 7/2006 | Lange et al. | |
| 7,081,095 B2 | 7/2006 | Lynn et al. | |
| 7,082,331 B1 | 7/2006 | Park et al. | |
| 7,082,336 B2 | 7/2006 | Ransbury et al. | |
| 7,087,053 B2 | 8/2006 | Vanney | |
| 7,104,965 B1 | 9/2006 | Jiang et al. | |
| 7,117,036 B2 | 10/2006 | Florio | |
| 7,128,717 B1 | 10/2006 | Thach et al. | |
| 7,149,573 B2 | 12/2006 | Wang | |
| 7,155,278 B2 | 12/2006 | King et al. | |
| 7,160,252 B2 | 1/2007 | Cho et al. | |
| 7,160,255 B2 | 1/2007 | Saadat | |
| 7,167,743 B2 | 1/2007 | Heruth et al. | |
| 7,174,215 B2 | 2/2007 | Bradley | |
| 7,186,220 B2 | 3/2007 | Stahmann et al. | |
| 7,189,204 B2 | 3/2007 | Ni et al. | |
| 7,200,440 B2 | 4/2007 | Kim et al. | |
| 7,212,862 B2 | 5/2007 | Park et al. | |
| 7,214,197 B2 | 5/2007 | Prass | |
| 7,216,000 B2 | 5/2007 | Sieracki et al. | |
| 7,252,640 B2 | 8/2007 | Ni et al. | |
| 7,269,549 B2 | 9/2007 | Koh | |
| 7,277,749 B2 | 10/2007 | Gordon | |
| 7,330,760 B2 | 2/2008 | Heruth et al. | |
| 7,336,996 B2 | 2/2008 | Hartley et al. | |
| 7,351,208 B2 | 4/2008 | Brodnick et al. | |
| 7,366,562 B2 | 4/2008 | Dukesherer | |
| 7,366,572 B2 | 4/2008 | Heruth et al. | |
| 7,395,113 B2 | 7/2008 | Heruth et al. | |
| 7,396,333 B2 | 7/2008 | Stahmann et al. | |
| 7,447,545 B2 | 11/2008 | Heruth et al. | |
| 7,463,928 B2 | 12/2008 | Lee et al. | |
| 7,468,040 B2 | 12/2008 | Hartley et al. | |
| 7,469,697 B2 | 12/2008 | Lee et al. | |
| 7,473,227 B2 | 1/2009 | Hsu et al. | |
| 7,491,181 B2 | 2/2009 | Heruth et al. | |
| 7,509,164 B2 | 3/2009 | Jensen et al. | |
| 7,510,531 B2 | 3/2009 | Lee et al. | |
| 7,515,968 B2 | 4/2009 | Metzler et al. | |
| 7,526,341 B2 | 4/2009 | Goetz et al. | |
| 7,542,803 B2 | 6/2009 | Heruth et al. | |
| 7,572,225 B2 | 8/2009 | Stahmann et al. | |
| 7,590,455 B2 | 9/2009 | Heruth et al. | |
| 7,591,265 B2 | 9/2009 | Lee et al. | |
| 7,596,413 B2 | 9/2009 | Libbus et al. | |
| 7,596,414 B2 | 9/2009 | Whitehurst et al. | |
| 7,599,730 B2 | 10/2009 | Hunter | |
| 7,603,170 B2 | 10/2009 | Hatlestad et al. | |
| 7,606,613 B2 | 10/2009 | Simon | |
| 7,610,094 B2 | 10/2009 | Stahmann et al. | |
| 7,634,315 B2 | 12/2009 | Cholette | |
| 7,644,714 B2 | 1/2010 | Atkinson et al. | |
| 7,657,308 B2 | 2/2010 | Miles et al. | |
| 7,662,105 B2 | 2/2010 | Hatlestad | |
| 7,672,728 B2 | 3/2010 | Libbus et al. | |
| 7,678,061 B2 | 3/2010 | Lee et al. | |
| 7,680,538 B2 | 3/2010 | Durand et al. | |
| 7,684,869 B2 | 3/2010 | Bradley et al. | |

(56) References Cited

U.S. PATENT DOCUMENTS

| | | | |
|---|---|---|---|
| 7,697,984 B2 * | 4/2010 | Hill | A61B 17/3417 607/9 |
| 7,702,385 B2 | 4/2010 | Moffitt et al. | |
| 7,717,848 B2 | 5/2010 | Heruth et al. | |
| 7,720,541 B2 | 5/2010 | Stahmann et al. | |
| 7,725,195 B2 | 5/2010 | Lima et al. | |
| 7,725,198 B2 | 5/2010 | Cross, Jr. et al. | |
| 7,726,209 B2 | 6/2010 | Ruotiout | |
| 7,734,340 B2 | 6/2010 | De Ridder | |
| 7,734,350 B2 | 6/2010 | Dubnov et al. | |
| 7,742,819 B2 | 6/2010 | Moffitt | |
| 7,747,323 B2 | 6/2010 | Libbus et al. | |
| 7,751,880 B1 | 7/2010 | Cholette | |
| 7,757,690 B2 | 7/2010 | Stahmann et al. | |
| 7,775,993 B2 | 8/2010 | Heruth et al. | |
| 7,783,353 B2 | 8/2010 | Libbus et al. | |
| 7,792,583 B2 | 9/2010 | Miesel et al. | |
| 7,792,590 B1 | 9/2010 | Pianca et al. | |
| 7,809,442 B2 | 10/2010 | Bolea et al. | |
| 7,818,063 B2 | 10/2010 | Wallace et al. | |
| 7,853,322 B2 | 12/2010 | Bourget et al. | |
| 7,881,798 B2 | 2/2011 | Miesel et al. | |
| 7,908,013 B2 | 3/2011 | Miesel et al. | |
| 7,917,230 B2 | 3/2011 | Bly | |
| 7,942,822 B1 | 5/2011 | Koh | |
| 7,957,797 B2 | 6/2011 | Bourget et al. | |
| 7,957,809 B2 | 6/2011 | Bourget et al. | |
| 7,979,128 B2 | 7/2011 | Tehrani et al. | |
| 8,016,776 B2 | 9/2011 | Bourget et al. | |
| 8,021,299 B2 | 9/2011 | Miesel et al. | |
| 8,150,531 B2 | 4/2012 | Skelton | |
| 8,160,711 B2 | 4/2012 | Tehrani et al. | |
| 8,175,720 B2 | 5/2012 | Skelton et al. | |
| 8,909,341 B2 * | 12/2014 | Gelfand | A61N 1/3601 607/42 |
| 2001/0010010 A1 | 7/2001 | Richmond et al. | |
| 2002/0010495 A1 | 1/2002 | Freed et al. | |
| 2002/0049479 A1 | 4/2002 | Pitts | |
| 2002/0120188 A1 | 8/2002 | Brock | |
| 2002/0128700 A1 | 9/2002 | Cross, Jr. | |
| 2002/0156507 A1 | 10/2002 | Lindenthaler | |
| 2002/0183791 A1 * | 12/2002 | Denker et al. | 607/5 |
| 2003/0093128 A1 | 5/2003 | Freed et al. | |
| 2003/0114895 A1 | 6/2003 | Gordon et al. | |
| 2003/0114905 A1 | 6/2003 | Kuzma | |
| 2003/0139789 A1 | 8/2003 | Tvinnereim | |
| 2003/0153953 A1 * | 8/2003 | Park et al. | 607/17 |
| 2003/0195571 A1 | 10/2003 | Burnes et al. | |
| 2003/0216789 A1 | 11/2003 | Deem et al. | |
| 2004/0015204 A1 | 1/2004 | Whitehurst et al. | |
| 2004/0111139 A1 | 1/2004 | McCreery | |
| 2004/0073272 A1 | 4/2004 | Knudson et al. | |
| 2004/0116819 A1 | 6/2004 | Alt | |
| 2004/0162499 A1 | 8/2004 | Nagai et al. | |
| 2004/0215288 A1 | 10/2004 | Lee et al. | |
| 2004/0230278 A1 | 11/2004 | Dahl et al. | |
| 2004/0260310 A1 | 12/2004 | Harris | |
| 2005/0004610 A1 | 1/2005 | Kim et al. | |
| 2005/0010265 A1 | 1/2005 | Baru Fassio et al. | |
| 2005/0085865 A1 | 1/2005 | Tehrani | |
| 2005/0042589 A1 | 2/2005 | Hatlestad et al. | |
| 2005/0043765 A1 | 2/2005 | Williams et al. | |
| 2005/0043772 A1 | 2/2005 | Stahmann et al. | |
| 2005/0076908 A1 | 4/2005 | Lee et al. | |
| 2005/0080348 A1 | 4/2005 | Stahmann et al. | |
| 2005/0080461 A1 | 4/2005 | Stahmann et al. | |
| 2005/0080472 A1 | 4/2005 | Atkinson et al. | |
| 2005/0081847 A1 | 4/2005 | Lee et al. | |
| 2005/0085866 A1 | 4/2005 | Tehrani | |
| 2005/0085868 A1 | 4/2005 | Tehrani et al. | |
| 2005/0085869 A1 | 4/2005 | Tehrani et al. | |
| 2005/0101833 A1 | 5/2005 | Hsu et al. | |
| 2005/0107838 A1 * | 5/2005 | Lovett et al. | 607/17 |
| 2005/0113710 A1 | 5/2005 | Stahmann et al. | |
| 2005/0115561 A1 | 6/2005 | Stahmann et al. | |
| 2005/0145246 A1 | 7/2005 | Hartley et al. | |
| 2005/0165457 A1 | 7/2005 | Benser et al. | |
| 2005/0197588 A1 * | 9/2005 | Freeberg | A61B 5/0031 600/529 |
| 2005/0209513 A1 | 9/2005 | Heruth et al. | |
| 2005/0209643 A1 | 9/2005 | Heruth et al. | |
| 2005/0234523 A1 | 10/2005 | Levin et al. | |
| 2005/0251216 A1 | 11/2005 | Hill et al. | |
| 2005/0261747 A1 | 11/2005 | Schuler et al. | |
| 2005/0267380 A1 | 12/2005 | Poezevara | |
| 2005/0267547 A1 | 12/2005 | Knudson et al. | |
| 2005/0277844 A1 | 12/2005 | Strother et al. | |
| 2005/0277999 A1 | 12/2005 | Strother et al. | |
| 2005/0278000 A1 | 12/2005 | Strother et al. | |
| 2006/0004429 A1 | 1/2006 | Mrva et al. | |
| 2006/0052836 A1 | 3/2006 | Kim et al. | |
| 2006/0058852 A1 | 3/2006 | Koh et al. | |
| 2006/0064029 A1 | 3/2006 | Arad (Abboud) | |
| 2006/0079802 A1 | 4/2006 | Jensen et al. | |
| 2006/0095088 A1 | 5/2006 | De Ridder | |
| 2006/0103407 A1 | 5/2006 | Kakizawa et al. | |
| 2006/0135886 A1 | 6/2006 | Lippert et al. | |
| 2006/0142815 A1 | 6/2006 | Tehrani et al. | |
| 2006/0167497 A1 | 7/2006 | Armstrong et al. | |
| 2006/0184204 A1 | 8/2006 | He | |
| 2006/0212096 A1 | 9/2006 | Stevenson | |
| 2006/0241708 A1 | 10/2006 | Boute | |
| 2002/0266369 | 11/2006 | Atkinson et al. | |
| 2006/0247729 A1 | 11/2006 | Tehrani et al. | |
| 2006/0259079 A1 | 11/2006 | King | |
| 2006/0264777 A1 | 11/2006 | Drew | |
| 2006/0266369 A1 | 11/2006 | Atkinson et al. | |
| 2006/0271137 A1 | 11/2006 | Stanton-Hicks | |
| 2006/0282127 A1 | 12/2006 | Zealear | |
| 2006/0293720 A1 | 12/2006 | DiLorenzo | |
| 2006/0293723 A1 | 12/2006 | Whitehurst et al. | |
| 2007/0027482 A1 | 2/2007 | Parnis et al. | |
| 2007/0150009 A1 * | 6/2007 | Kveen et al. | 607/9 |
| 2007/0233204 A1 | 10/2007 | Lima et al. | |
| 2007/0255379 A1 * | 11/2007 | Williams et al. | 607/120 |
| 2008/0027502 A1 * | 1/2008 | Ransom | A61B 5/036 607/42 |
| 2008/0039904 A1 | 2/2008 | Bulkes | |
| 2008/0046055 A1 | 2/2008 | Durand et al. | |
| 2008/0064977 A1 | 3/2008 | Kelleher et al. | |
| 2008/0097187 A1 | 4/2008 | Gielen | |
| 2008/0103407 A1 * | 5/2008 | Bolea et al. | 600/529 |
| 2008/0103545 A1 | 5/2008 | Bolea et al. | |
| 2008/0103570 A1 | 5/2008 | Gerber | |
| 2008/0109046 A1 | 5/2008 | Lima et al. | |
| 2008/0109048 A1 | 5/2008 | Moffitt | |
| 2008/0132802 A1 | 6/2008 | Ni et al. | |
| 2008/0139930 A1 | 6/2008 | Weese | |
| 2008/0167695 A1 * | 7/2008 | Tehrani et al. | 607/42 |
| 2008/0183187 A1 | 7/2008 | Bly | |
| 2008/0183254 A1 | 7/2008 | Bly et al. | |
| 2008/0208282 A1 | 8/2008 | Gelfand et al. | |
| 2008/0269602 A1 | 10/2008 | Csavoy | |
| 2008/0294060 A1 | 11/2008 | Haro et al. | |
| 2008/0312725 A1 * | 12/2008 | Penner | 607/119 |
| 2009/0024047 A1 | 1/2009 | Shipley et al. | |
| 2009/0036947 A1 | 2/2009 | Westlund et al. | |
| 2009/0062882 A1 | 3/2009 | Zhang et al. | |
| 2009/0112116 A1 | 4/2009 | Lee et al. | |
| 2009/0118787 A1 | 5/2009 | Moffitt | |
| 2009/0234427 A1 | 9/2009 | Chinn | |
| 2009/0287279 A1 | 9/2009 | Parramon et al. | |
| 2009/0270707 A1 | 10/2009 | Alfoqaha et al. | |
| 2009/0308395 A1 | 12/2009 | Lee et al. | |
| 2009/0326408 A1 | 12/2009 | Moon | |
| 2010/0010566 A1 | 1/2010 | Thacker et al. | |
| 2010/0036285 A1 | 2/2010 | Govari et al. | |
| 2010/0076536 A1 | 3/2010 | Merz et al. | |
| 2010/0094379 A1 | 4/2010 | Meadows et al. | |
| 2010/0125314 A1 | 5/2010 | Bradley et al. | |
| 2010/0125315 A1 | 5/2010 | Parramon et al. | |
| 2010/0137931 A1 | 6/2010 | Hopper et al. | |
| 2010/0137949 A1 | 6/2010 | Mazgalev et al. | |
| 2010/0137956 A1 | 6/2010 | Osypka | |

(56) References Cited

U.S. PATENT DOCUMENTS

| | | |
|---|---|---|
| 2010/0152553 A1 | 6/2010 | Ujhazy et al. |
| 2010/0174341 A1 | 7/2010 | Bolea et al. |
| 2010/0198103 A1 | 8/2010 | Meadows et al. |
| 2010/0228317 A1 | 9/2010 | Libbus et al. |
| 2010/0241195 A1 | 9/2010 | Meadows et al. |
| 2010/0241207 A1 | 9/2010 | Bluger |
| 2010/0262210 A1 | 10/2010 | Parramon et al. |
| 2011/0093036 A1 | 4/2011 | Mashiach |
| 2011/0112601 A1 | 5/2011 | Meadows et al. |
| 2011/0152965 A1 | 6/2011 | Mashiach et al. |

FOREIGN PATENT DOCUMENTS

| | | |
|---|---|---|
| SU | 925349 | 5/1982 |
| WO | 2004064634 | 8/2004 |
| WO | 2006047264 | 5/2006 |
| WO | 2006057734 | 6/2006 |
| WO | 2007092330 | 8/2006 |
| WO | 2007068284 | 6/2007 |
| WO | 2007078997 | 7/2007 |
| WO | 2008048471 | 4/2008 |
| WO | 2008115507 | 9/2008 |
| WO | 2009048580 | 4/2009 |
| WO | 2009048581 | 4/2009 |
| WO | 2009135138 | 11/2009 |
| WO | 2009135140 | 11/2009 |
| WO | 2009135142 | 11/2009 |
| WO | 2009140636 | 11/2009 |
| WO | 2010059839 | 5/2010 |
| WO | 2010117810 | 10/2010 |

OTHER PUBLICATIONS

Oliven Article—Arie Oliven et al., "Upper airway response to electrical stimulation of the genioglossus in obstructive sleep apnea," Journal of Applied Physiology, vol. 95, pp. 2023-2029, Nov. 2003, www.jap.physiology.org on Sep. 18, 2006. (8 pages).

Schwartz Article—Alan R. Schwartz MD et al., Theraputic Electrical Stimulation of the Hypoglossal Nerve in Obstructive Sleep Apnea, Arch Otolaryngol Head And Neck Surg., vol. 127, Oct. 2001, pp. 1216-1223. Copyright 2001 American Medical Association. (8 pages).

Mann Article—Eric A. Mann, MD, PhD et al., "The Effect of Neuromuscular Stimulation of the Genioglossus on the Hypopharyngeal Airway," The American Laryngouogical, Rhinological and Otological Society, Inc., 2002, pp. 351-356.

Park, "Preoperative Percutaneous Cranial Nerve Mapping in Head and Neck Surgery," Arch Facial Plast Surg/vol. 5, Jan./Feb. 2003, www.archfacial.compages 86-91.

Medtronic, The O-ARM Imaging System, Medtronic website, 2006-2007, 5 pages.

Medtronic, Stealth Station S7, "See the Bigger Picture", Medtronic website, Apr. 2008, 2 pages.

Van Buyten, et al., "Percutaneous technique for the treatment of Trigeminal Neuralgia becomes more precise and safer with the use of new Electromagnetic (EM) Navigation Technology", Nov. 1994, 6 pages.

Medtronic, "Navigation Tracking Technologies", Medtronic website, Dec. 28, 2008, 1 page.

Medtronic, "Intracardiac Navigation System", Medtronic website, Dec. 17, 2009, 2 pages.

\* cited by examiner

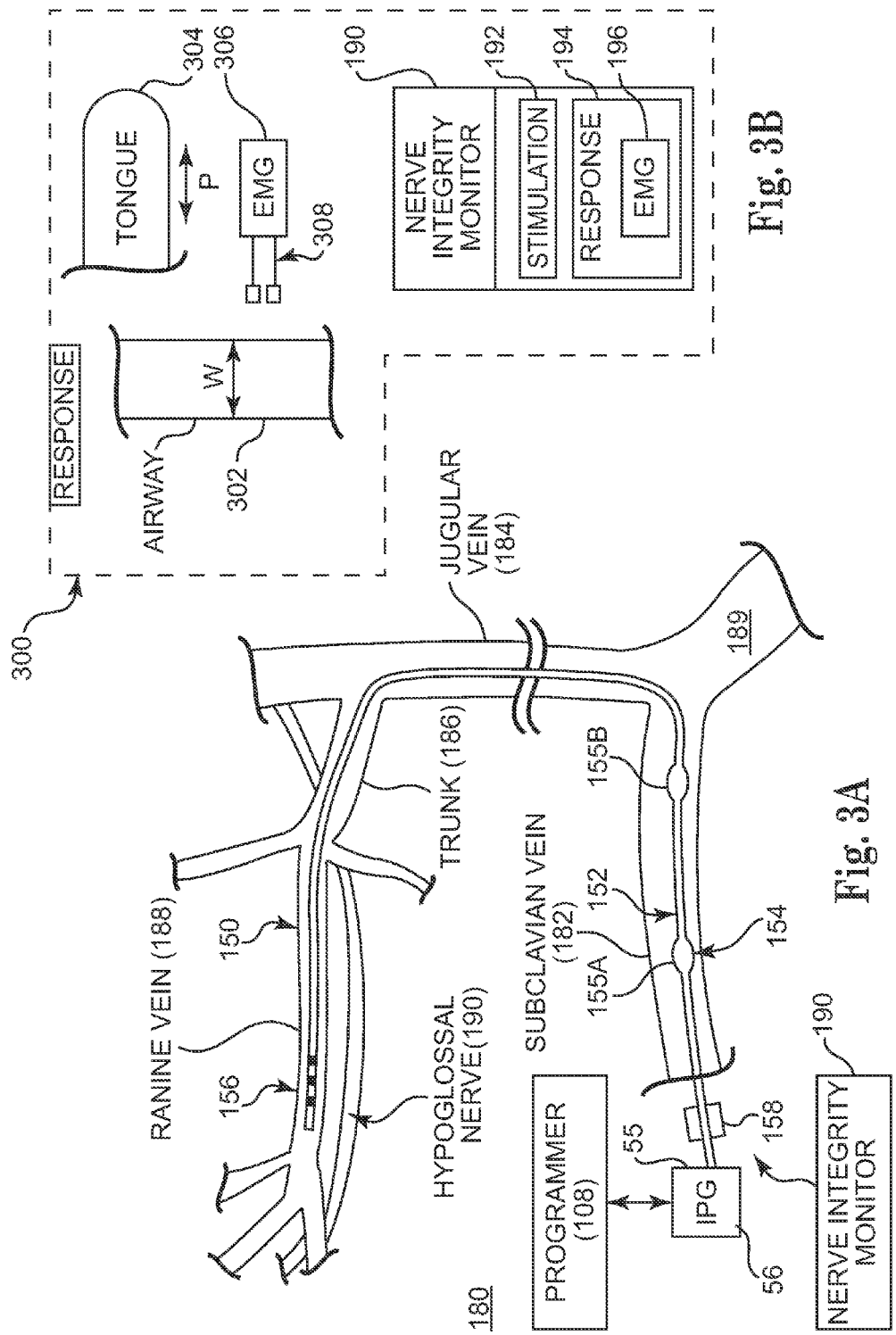

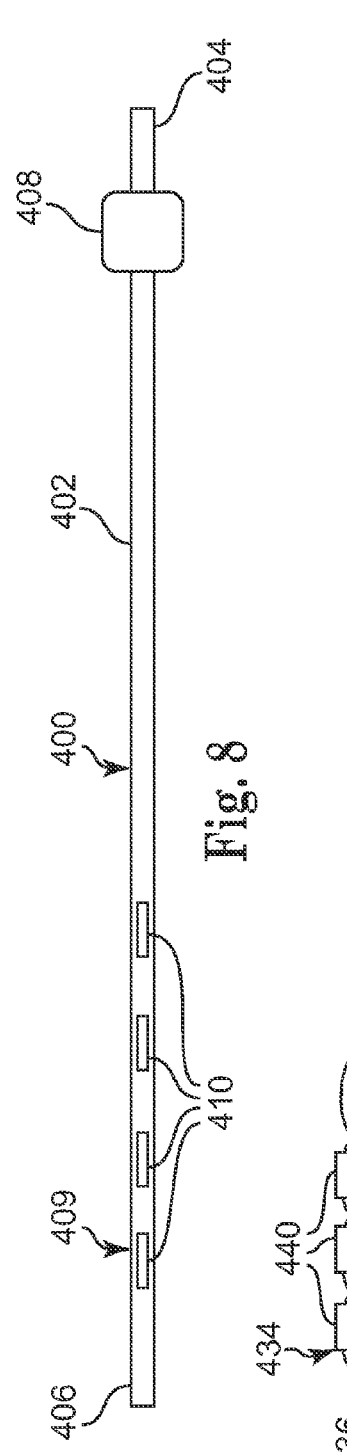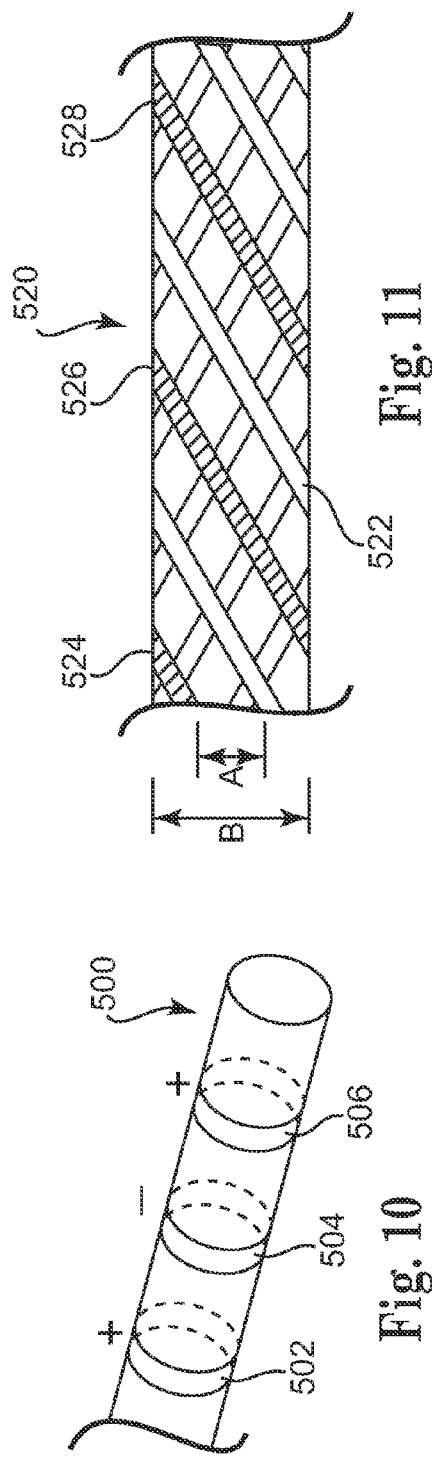

VIEW A-A

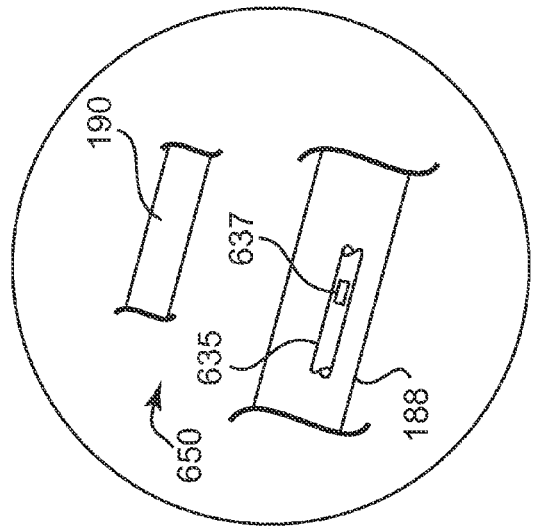
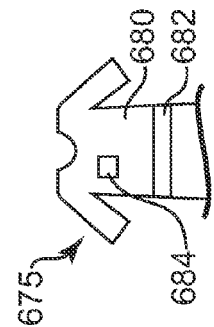
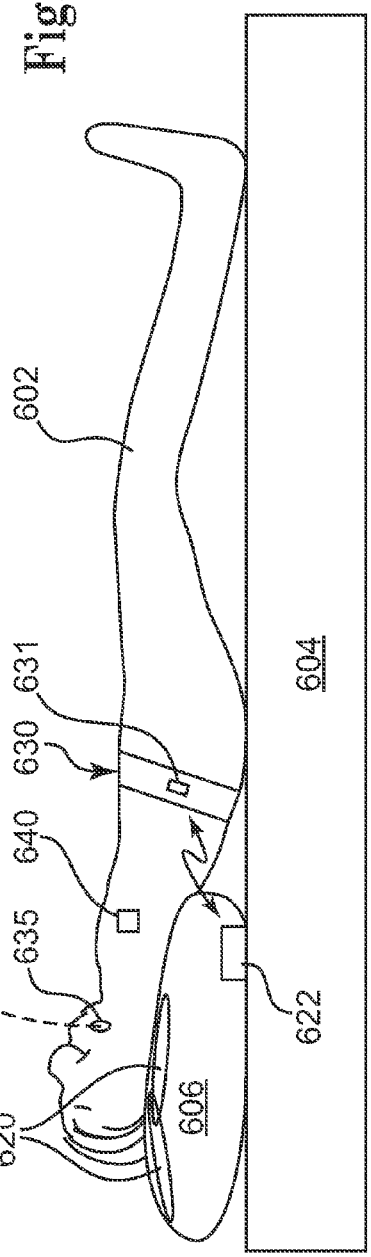
Fig. 15B
Fig. 15C
Fig. 15A

TRANSVENOUS METHOD OF TREATING SLEEP APNEA

CROSS-REFERENCE TO RELATED APPLICATIONS

This Utility patent application is a U.S. National Stage filing under 35 U.S.C. § 371 of PCT/US2009/59060, filed Sep. 30, 2009 and U.S. Provisional Application No. 61/101,952, filed Oct. 1, 2008, both of which are incorporated herein by reference.

BACKGROUND

The present disclosure relates generally to an implantable stimulation system for stimulating and monitoring soft tissue in a patient, and more particularly, the present disclosure relates to a method of using a transvenous delivery of a stimulation lead to treat sleep apnea.

Sleep apnea generally refers to the cessation of breathing during sleep. One type of sleep apnea, referred to as obstructive sleep apnea (OSA), is characterized by repetitive pauses in breathing during sleep due to the obstruction and/or collapse of the upper airway, and is usually accompanied by a reduction in blood oxygenation saturation.

One treatment for obstructive sleep apnea has included the delivery of electrical stimulation to the hypoglossal nerve, located in the neck region under the chin. Such stimulation therapy activates the upper airway muscles to maintain upper airway patency. In treatment of sleep apnea, increased respiratory effort resulting from the difficulty in breathing through an obstructed airway is avoided by synchronized stimulation of an upper airway muscle or muscle group that holds the airway open during the inspiratory phase of breathing. For example, the genioglossus muscle is stimulated during treatment of sleep apnea by a cuff electrode placed around the hypoglossal nerve.

BRIEF DESCRIPTION OF THE DRAWINGS

Aspects and features of the present disclosure will be appreciated as the same becomes better understood by reference to the following detailed description of the embodiments of the present disclosure when considered in connection with the accompanying drawings, wherein:

FIG. 3A is a schematic illustration of a transvenous placement of a stimulation lead and sensor for treating sleep apnea, according to an embodiment of the present disclosure;

FIG. 3B is a schematic illustration of an array of response evaluation tools and a nerve monitoring system, according to an embodiment of the present disclosure;

FIG. 8 is a side plan view of a stimulation lead, according to an embodiment of the present disclosure;

FIG. 9 is a side plan view of a stimulation lead including a coiled configuration at a distal portion, according to an embodiment of the present disclosure;

FIG. 10 is a perspective view of a distal portion of a stimulation lead including an array of ring electrodes, according to an embodiment of the present disclosure;

FIG. 11 is a side plan view of a distal portion of a stimulation lead including a combined stent-electrode configuration, according to an embodiment of the present disclosure;

FIG. 15A is a side plan view schematically illustrating a nerve stimulation system, according to an embodiment of the present disclosure;

FIG. 15B is a schematic illustration of a transvenous placement of a microstimulator of the system of FIG. 15A, according to an embodiment of the present disclosure;

FIG. 15C is a schematic illustration of a garment configured to provide respiratory sensing for the system of FIGS. 15A-15B, according to an embodiment of the present disclosure;

DESCRIPTION OF EMBODIMENTS

The following detailed description is merely exemplary in nature and is not intended to limit the present disclosure or the application and uses of the present disclosure. Furthermore, there is no intention to be bound by any expressed or implied theory presented in the preceding technical field, background, or the following detailed description.

Embodiments of the present disclosure provide an implantable medical device for treating obstructive sleep apnea wherein stimulation is provided to the hypoglossal nerve (or another target nerve) through a transvenous lead system. The stimulation may be provided synchronous with respiration detected by a sensing lead system. In some embodiments, a single transvenous lead includes both a sensing lead and the stimulation lead, such that the sensing lead is integral with or connected to the stimulation lead. In other embodiments, the sensing lead forms a transvenous lead separate from a transvenous stimulation lead. In still other embodiments, the sensing lead comprises a sensing lead external to the venous system altogether (such as being mounted externally on a patient or subcutaneously implanted) while the stimulation lead comprises a transvenous lead.

Figure 1:
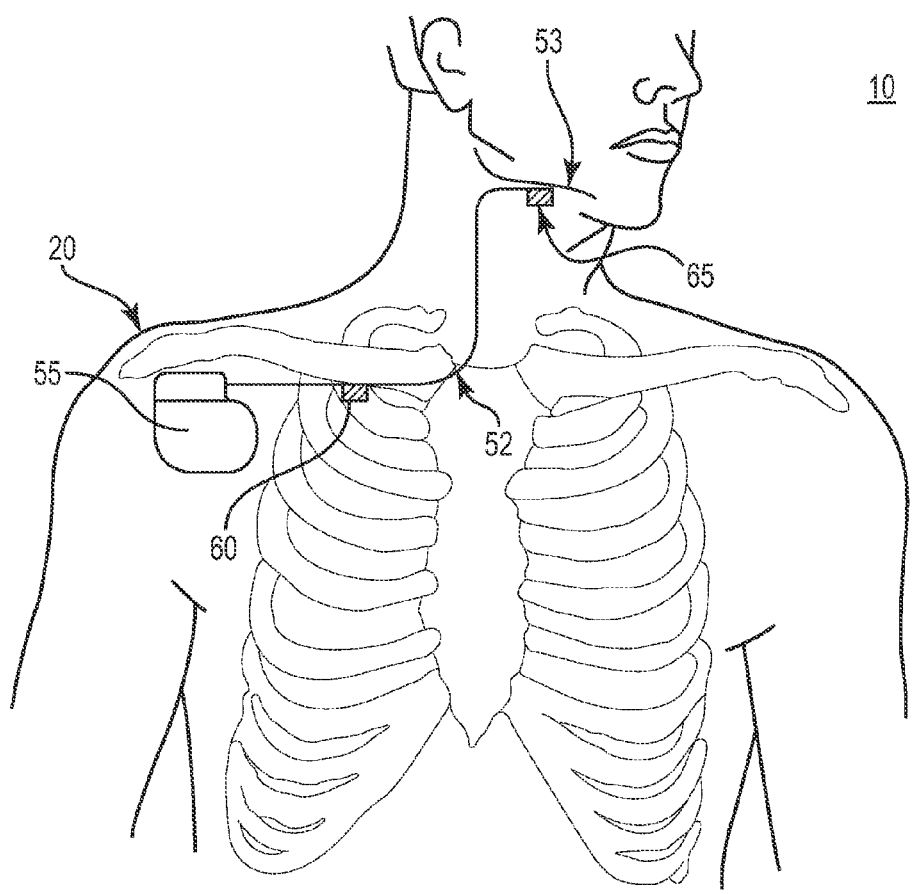
FIG. 1 is a schematic illustration of an implantable stimulation system, according to an embodiment of the present disclosure.

FIG. 1 is a schematic diagram of an implantable stimulation system that includes a transvenously placed stimulation electrode, according to an embodiment of the present disclosure. As illustrated in FIG. 1, an example of an implantable stimulation system 10 according to one embodiment of the present disclosure includes an implantable pulse generator (IPG) 55, capable of being surgically positioned within a pectoral region of a patient 20, and a stimulation lead 52 electrically coupled with the IPG 55 via a connector (not shown) positioned within a connection port of the IPG 55. The lead 52 includes a stimulation electrode portion 65 and extends from the IPG 55 so that the stimulation electrode portion 65 is positioned within a portion of the vasculature adjacent a desired nerve, such as the hypoglossal nerve 53 of the patient 10, to enable stimulation of the nerve 53, as described below in detail. An exemplary implantable stimulation system in which lead 52 may be utilized, for example, is described in U.S. Pat. No. 6,572,543 to Christopherson et al., and which is incorporated herein by reference in its entirety. In one embodiment, the lead 52 further includes an sensor portion 60 (electrically coupled to the IPG 55 and extending from the IPG 55) positioned in the patient 10 for sensing respiratory effort.

In some embodiments, in addition to the IPG 55 being configured to treat obstructive sleep apnea, the IPG 55 is additionally configured as a cardiac therapy device, such as a bradycardia pacemaker, implantable cardiac defibrillator, or cardiac resynchronization therapy device. In one aspect, one or more leads extend from the IPG 55 to access the heart via a transvenous approach in order to apply a cardiac therapy. In one embodiment, one or more of these cardiac therapy configurations of the IPG 55 also have sensors (pressure, impedance) on the cardiac leads which may also provide a respiratory signal for use in delivering an obstructive sleep apnea therapy. Exemplary embodiments of an implantable stimulation system for applying a cardiac therapy via transvenous delivery of a lead is described in Hill et al. U.S. Pat. No. 6,006,134 and Cho et al. U.S. Pat. No. 6,641,542, which are both incorporated by reference herein in their entirety.

In one embodiment in which the IPG 55 is configured to treat both cardiac therapy and sleep apnea, a first lead (or set of leads) extends from the IPG 55 for sensing cardiac activity and detecting cardiac events while a second lead (or set of leads) extends from the IPG 55 to sense respiratory activity and to detect respiratory events. However, in another embodiment, only one set of leads is used to sense both respiratory activity and cardiac activity. Accordingly, in this latter embodiment, in one configuration, a respiratory signal obtained via a cardiac sensing lead is also used to trigger application of a stimulation signal when applying an obstructive sleep apnea therapy, and also optionally is used to monitor and detect apneas.

In some embodiments, instead of using a single IPG to apply both cardiac therapies and sleep apnea therapies, a second implantable pulse generator (IPG 55) is implanted (in addition to the first IPG) so that one IPG 55 applies a cardiac therapy while the other IPG 55 applies an obstructive sleep apnea therapy.

Figure 2A:
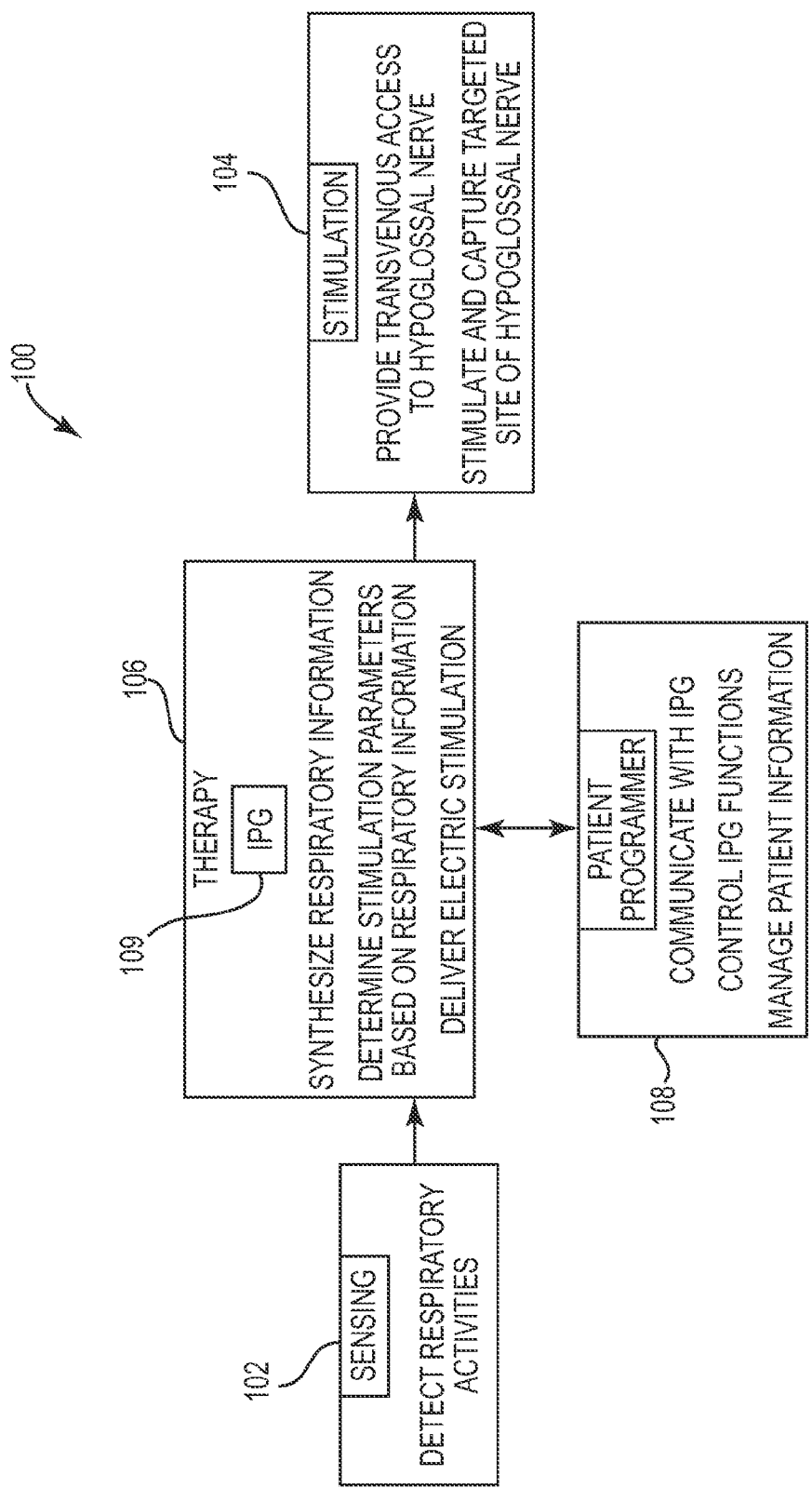
FIG. 2A is a schematic illustration of a block diagram of an implantable stimulation system, according to an embodiment of the present disclosure.

FIG. 2A is a block diagram schematically illustrating an implantable stimulation system 100, according to one embodiment of the present disclosure. In one embodiment, system 100 comprises at least substantially the same features and attributes as system 10 of FIG. 1. As illustrated in FIG. 2A, system 100 includes a sensing module 102, a stimulation module 104, a therapy module 106, and a patient management module 108. In one embodiment, the IPG 109 of therapy module 106 comprises at least substantially the same features and attributes as IPG 55 of FIG. 1.

Via an array of parameters, the sensing module 102 receives and tracks signals from various physiologic sensors (such as a pressure sensor, blood oxygenation sensor, acoustic sensor, electrocardiogram (ECG) sensor, or impedance sensor) in order to determine a respiratory state of a patient, whether or not the patient is asleep or awake, and other respiratory-associated indicators, etc. Such respiratory detection may be received from either a single sensor or any multiple of sensors, or combination of various physiologic sensors which may provide a more reliable and accurate signal.

Figure 2B:
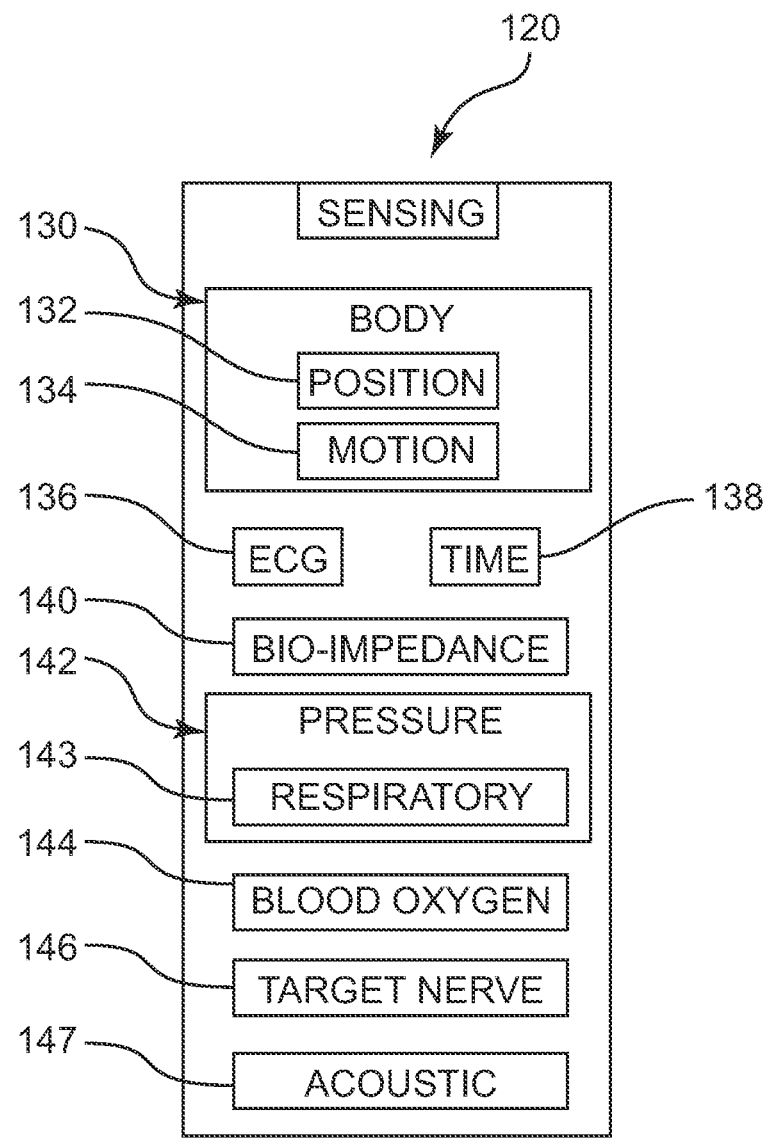
FIG. 2B is a schematic illustration of a block diagram of a sensing monitor, according to an embodiment of the present disclosure.

For example, in one embodiment, the sensing module 102 comprises a sensing monitor 120, as illustrated in FIG. 2B. The sensing monitor 120 includes a body parameter 130, which includes at least one of a position-sensing component 132 or a motion-sensing component 134. In one embodiment, the motion-sensing component 134 tracks sensing of "seismic" activity (via an accelerometer or a piezoelectric transducer) that is indicative of walking, body motion, talking, etc. In another embodiment, the position-sensing component 132 tracks sensing of a body position or posture via an accelerometer or other transducer. In some embodiments, body parameter 130 utilizes signals from both the position-sensing component 132 and the motion-sensing component 134.

In some embodiments, sensing monitor 120 additionally comprises one or more of the following parameters: an ECG parameter 136; a time parameter 138; a bio-impedance parameter 140; a pressure parameter 142; and a blood oxygen parameter 144. In one aspect, the pressure parameter 142 includes a respiratory pressure component 143. In one aspect, the time parameter 142 tracks time generally (e.g. time intervals, elapsed time, etc.) while in other aspects, the time parameter 142 tracks the time of day in addition to or instead of the general time parameters. In another aspect, the time parameter 142 can be used to activate or deactivate a therapy regimen according to a time of day.

It is also understood that system 100 (FIG. 2A) would include, or be connected to, the analogous physiologic sensor (e.g., LED-type tissue perfusion oxygen saturation) implanted within or attached to the body of the patient to provide data to each one of their respective parameters (e.g., blood oxygenation parameter 144) of the sensing monitor 120. In some embodiments, sensing monitor 120 also includes a target nerve parameter 146 which represents physiologic data regarding the activity of a nerve to be stimulated, such as the hypoglossal nerve, including specification of the trunk and/or one or more branches of the hypoglossal nerve.

In other embodiments, the target nerve comprises another nerve (other than the hypoglossal nerve) that facilitates a therapy regimen to treat obstructive sleep apnea. In yet other embodiments, sensing monitor 120 also includes an acoustic sensing parameter 147 which represents physiologic data from respiratory airflow or cardiac activity that is sensed acoustically and that is indicative of respiratory effort.

In further reference to FIG. 2A, therapy manager 106 of system 100 is configured to automatically control initiation, termination, and/or adjustment of a sleep apnea therapy, in accordance with the principles of the present disclosure. Therapy manager 106 also tracks and applies various treatment parameters, such as an amplitude, pulse width, electrode polarity, duration, and/or frequency of a neuro-stimulation signal, in accordance with a treatment protocol programmed into the therapy manager 106.

In one embodiment, therapy manager 106 comprises one or more processing units and associated memories configured to generate control signals directing the operation of system 100, including at least sensing module 102, therapy manager 106, stimulation module 104, and patient management module 108. In particular, in response to or based upon commands received via an input and/or instructions contained in the memory associated with the controller in response to physiologic data gathered via the sensing module 102, therapy manager 106 generates control signals directing operation of stimulation module 104 to selectively control stimulation of a target nerve, such as the hypoglossal nerve, to restore airway patency and thereby reduce or eliminate apneic events.

With this in mind, therapy manager 106 acts to synthesize respiratory information, to determine suitable stimulation parameters based on that respiratory information, and to direct electrical stimulation to the target nerve. While any number of physiologic parameters can be used with varying success to detect an apnea, in one embodiment of the present disclosure, the sensing module 102 detects apneas via a thoracic bio-impedance parameter. In particular, a measurement of thoracic impedance is used to track the relative amplitude of the respiratory waveform. Physiologically speaking, the bio-impedance of the lungs varies as the lungs fill and empty with air. Accordingly, thoracic impedance increases during inspiration and decreases during expiration. In another aspect, a varying respiratory drive will also cause the amplitude of the bio-impedance to vary, with a larger respiratory drive increasing the signal amplitude of the bio-impedance. In one embodiment, the vector providing the bio-impedance measurement is predominantly lung-volume related, and not due to diaphragm displacement or cardiac displacement during respiration.

Upon obtaining the bio-impedance signal, the bio-impedance signal is further processed to identify an average peak amplitude over time. An apnea is detected by further identifying cyclic amplitude variations that occur for a duration substantially similar to the already known duration of a typical apneic event.

For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage, as represented by a memory associated with the controller. In other embodiments, hard wired circuitry may be used in place of or in combination with software instructions to implement the functions described. For example, the controller may be embodied as part of one or more application-specific integrated circuits (ASICs). Unless otherwise specifically noted, the controller is not limited to any specific combination of hardware circuitry and software, nor limited to any particular source for the instructions executed by the processing unit.

In general terms, the stimulation module 104 of system 100 is configured to generate and apply a neuro-stimulation signal via electrode(s) (such as stimulation electrode(s) 65) according to a treatment regimen programmed by a physician and/or in cooperation with therapy manager 106.

In general terms, the patient management module 108 is configured to facilitate communication to and from the IPG 109 in a manner familiar to those skilled in the art. Accordingly, the patient management module 108 is configured to report activities of the IPG 109 (including sensed physiologic data, stimulation history, number of apneas detected, etc.) and is configured to receive initial or further programming of the IPG 109 from an external source, such as a patient programmer, clinician programmer, etc.

FIG. 3A schematically illustrates a lead 150 in one exemplary embodiment of the implantable stimulation system 10 of FIG. 1. As shown in FIG. 3A, lead 150 is configured to be delivered transvenously and to be positioned within the vasculature. Lead 150 is configured to place a stimulation electrode portion 156 within the ranine vein 188 adjacent the hypoglossal nerve 190 (or another vein adjacent the hypoglossal nerve or another target nerve). In one aspect, the ranine vein is the vena comitans of the hypoglossal nerve, which begins at its distal end at a point below the front of the tongue, travels along the distal portion of the hypoglossal nerve, and then may join the lingual vein, and eventually opens into the internal jugular vein. In another aspect, other veins, such as another branch of the lingual vein may also be a candidate for the simulation electrode placement instead of the ranine vein or in addition to the ranine vein.

Accordingly, lead 150 is employable in a method of transvenously delivering a stimulation electrode to stimulate a target nerve. In this method, as illustrated in FIG. 3A, lead 150 is introduced into and through the subclavian vein 182 and then is advanced through the jugular vein 184, through vein trunk 186, and into the ranine vein 190 (otherwise known as the vein comitans of the hypoglossal nerve) until stimulation electrode portion 156 is within a desired position of the ranine vein 180 (or another vein adjacent a target nerve).

Figure 4A:
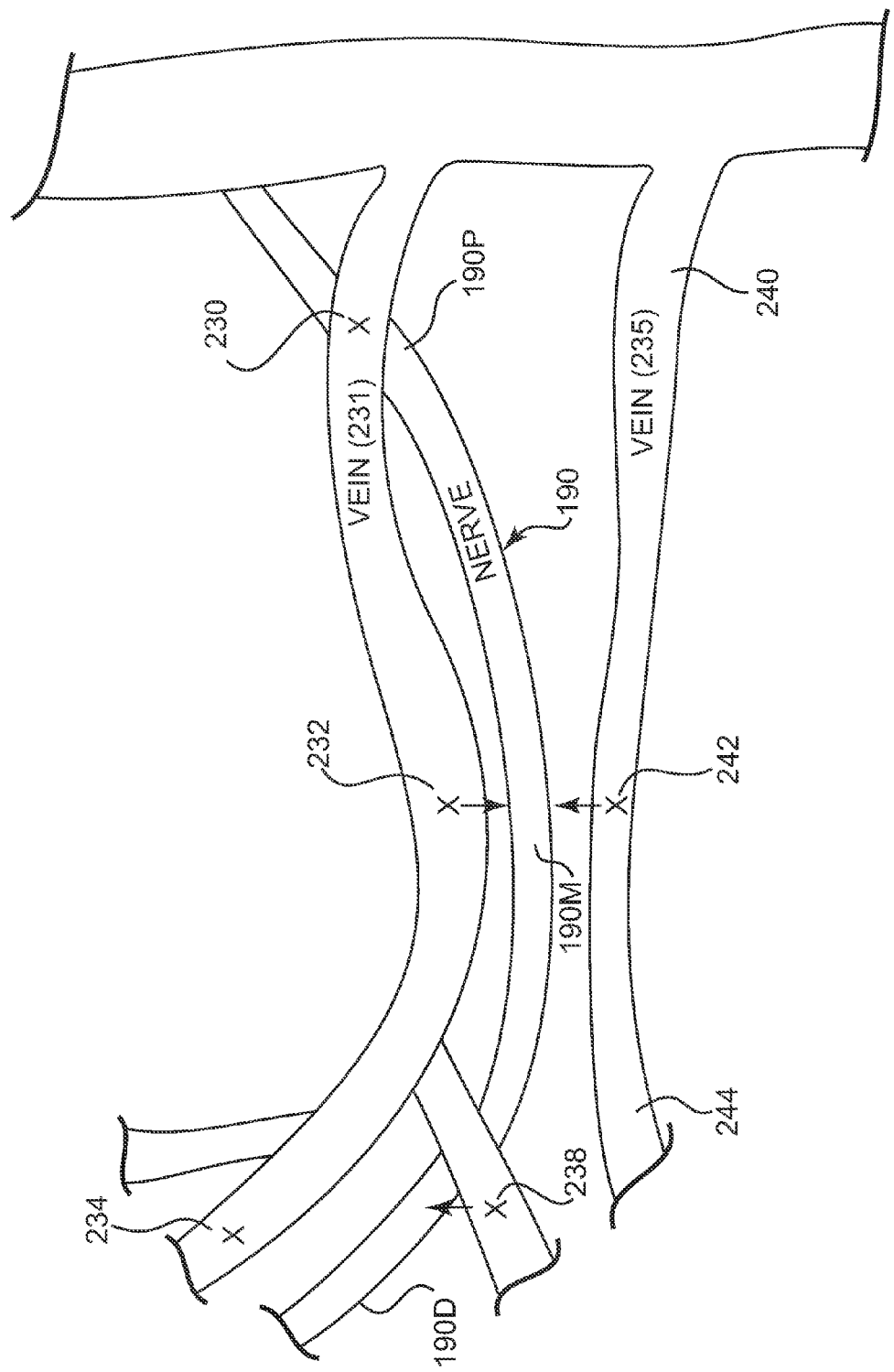
FIG. 4A is a schematic illustration of a method of stimulating a nerve via multiple venous pathways and/or via multiple stimulation sites, according to an embodiment of the present disclosure.

In some embodiments, the neuro-stimulation signal is applied at a single stimulation site along the hypoglossal nerve or another target nerve, as illustrated in FIG. 3A. However, in other embodiments, the neuro-stimulation signal of a sleep apnea therapy is applied from one or more of multiple locations 230, 232, 234, 240, 242, 244 (represented by the symbol x) within one or more veins to target multiple stimulation sites 190P, 190M, 190D along a target nerve 190, as schematically illustrated in FIG. 4A. The electric field applied at each site is represented schematically by the directional arrow extending from the symbol x toward the stimulation site 190M, 190P, 190D on nerve 190. In one aspect, these multiple sites include multiple stimulation locations arranged proximally (e.g., location 230), midway (e.g. location 232), and distally (e.g., location 234) within vein 231 along the hypoglossal nerve 190, one or more stimulation locations on both the right and left hypoglossal nerves, and/or multiple stimulation locations (proximal 240, midportion 242, and distal 244) along another vein 235 adjacent to the hypoglossal nerve 190. While FIG. 4A depicts three stimulation sites or regions 190P, 190M, 190P on the target nerve, it is understood that embodiments of the present disclosure are employable to stimulate nerve 190 at any point (or multiple points) between (or distally beyond or proximally beyond) the identified regions 190P, 190M, 190P along nerve 190.

Figure 4B:
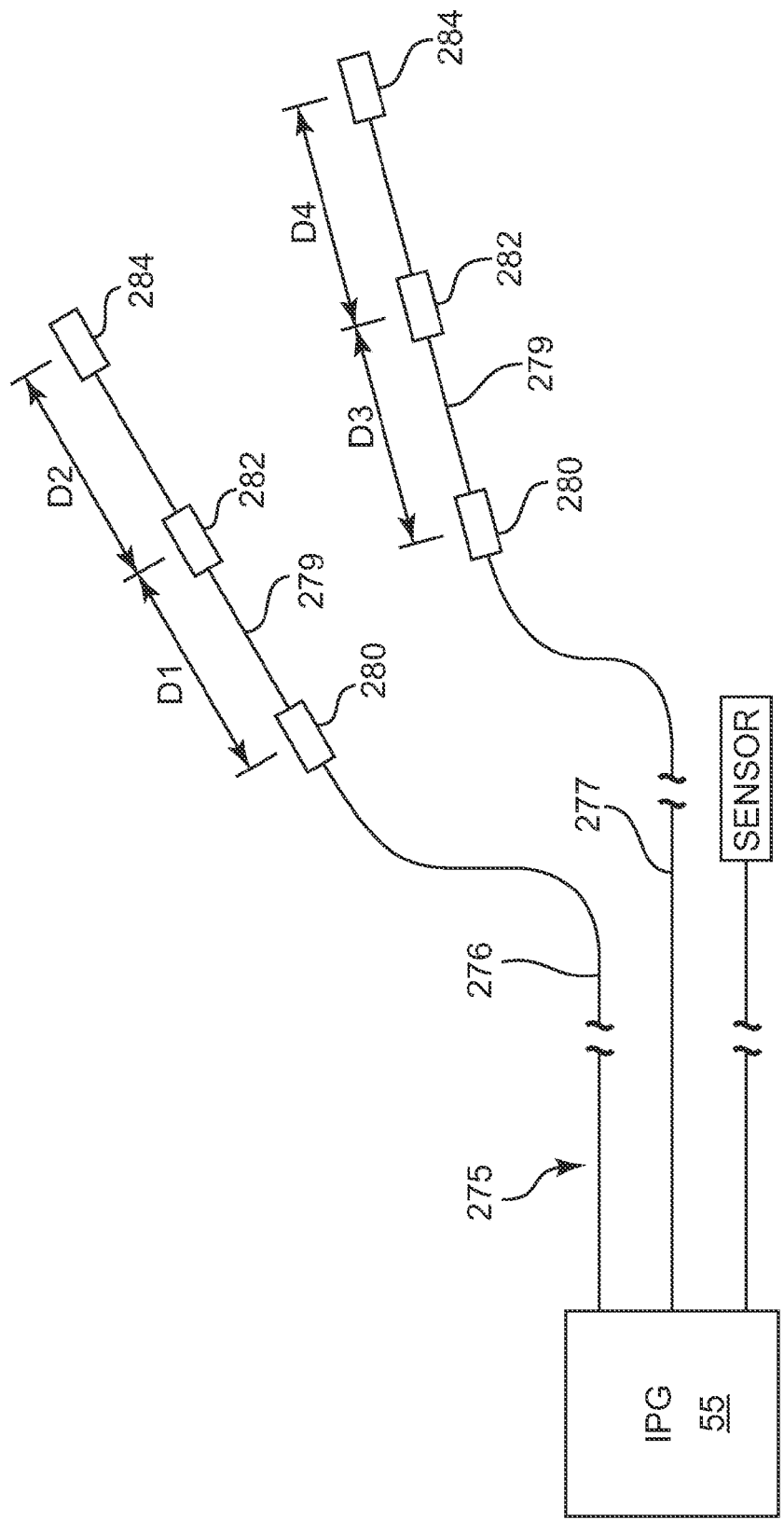
FIG. 4B is a schematic illustration of a stimulation lead system including multiple independent stimulation leads, according to an embodiment of the present disclosure.

It is understood, as illustrated in FIG. 4B, that in some embodiments, a stimulation lead system 275 includes two or more stimulation leads 276,277 that extend from an IPG 55 (FIGS. 1-2) to enable the separate leads 276,277 to extend down each of the respective different transvenous pathways to enable two or more independent stimulation locations on a single target nerve from different veins, such as veins 231 and 235 (FIG. 2). In one aspect, each separate lead includes one, two, or more different electrode portions 280, 282, 284 spaced apart from each other along a length of the distal portion 279 of each lead 276, 277, as further illustrated in FIG. 4B. In some embodiments, the electrode portions 280, 282, 284 of each lead 276, 277 are arranged with a minimum distance (D1 or D2) therebetween such that the stimulation signal applied at one electrode portion is separate and independent from the stimulation signal applied at the other electrode portions to achieve independent stimulation sites along the same target nerve. Accordingly, the electrode portions of a distal portion of one lead are spaced apart such that when a stimulation signal from a first electrode portion (e.g., electrode portion 280) is applied at one site, the other respective sites are not stimulated by the first electrode portion. Of course, it is also understood that each of the electrode portions 280, 282, 284 can be activated simultaneously to simultaneously apply a signal to each of the spaced apart, independent stimulation sites.

In some embodiments, the spacing D1 and D2 between the electrodes on the first lead 276 is equal to each other and the spacing D3 and D4 between the electrodes on the second lead 277 is equal to each other. In some other embodiments, the spacing D1 and D2 between the electrodes on the first lead 276 (or the spacing D3 and D4 between the electrodes on the second lead 277) is substantially different from each other. In some embodiments, the spacing (D1, D2) between the electrodes on the first lead 276 is the same as the spacing (D3, D4) between the respective electrode portions on the second lead 277. However, in other embodiments, the spacing (D1, D2) between the electrodes on the first lead 276 are the different than the spacing (D3, D4) between the electrode portions on the second lead 277 to account for the different distances traveled transvenously by the respective leads 276, 277 to locate the different respective electrode portions at desired stimulation sites.

It is understood that in other embodiments, the transvenously accessible stimulation sites along one or more nerves are spaced apart from each other by a distance that requires the application of stimulation signals to enable capturing the corresponding portion of the target nerve but wherein the spacing between adjacent stimulation sites along the nerve is close enough to allow some overlap between the adjacent stimulation signals.

In some embodiments, the separate stimulation leads 276, 277 of transvenous lead system 275 are positioned transvenously within different veins (e.g., 231 and 235 or a different set of veins) to stimulation different nerves. In this arrangement, one transvenous lead 276 stimulates a first nerve (such as nerve 190) and the other transvenous lead 277 stimulates a second nerve (not shown). In one aspect, each of the first and second nerves are associated with control of the respiratory system such that their selective stimulation relative to a respiratory pattern restores and maintains airway patency to alleviate obstructive sleep apnea.

Referring again to FIG. 3A, in some embodiments a nerve integrity monitor (stand alone monitor 190 or integrated into a sleep apnea physician programmer 108, such as programmer 108 in FIG. 2) is used to aide the physician in placing the electrode portion 156 of lead 150 in the proper location. In this regard, in one embodiment, the nerve integrity monitor comprises at least substantially the same features and attributes as the nerve integrity monitor described in U.S. Pat. No. 6,334,068, entitled INTRAOPERATIVE NEUROELECTROPHYSIOLOGICAL MONITOR, issued on Dec. 25, 2001, and which is hereby incorporated by reference in its entirety. In other embodiments, other nerve integrity monitors or an equivalent array of instruments (e.g., a stimulation probe and electromyography system) are used to apply the stimulation signal and evaluate the response of the muscle innervated by the target nerve.

In one embodiment, nerve integrity monitor 190 is further illustrated in FIG. 3B and comprises stimulation module 192 and a response module 194 that includes electromyography monitoring electronics (EMG) 196.

With this in mind, FIG. 3B further illustrates a response evaluation array 300, according to one embodiment of the present disclosure. As shown in FIG. 3B, response evaluation array 300 provides one or more mechanisms to evaluate the effectiveness of a target site for stimulating a target nerve. In one embodiment, the array 300 includes: (1) observing or measuring the extent and location (an extension of the base of the tongue is preferred over extension of the tip) of tongue motor response 304, such as but not limited to tongue protrusion (indicated by arrow P); (2) observing or measuring the extent of increased cross-sectional area (indicated by arrow W) of an upper respiratory airway 302; (3) measuring the extent of an EMG response 306 (measured via EMG electronics 196 of monitor 190) of one or more muscles upon stimulation applied at a potential target site within a vein; (4) observing or detecting a twitch of the tongue or laryngeal muscle; and/or (5) a substantial reduction in apnea events.

Accordingly, with this in mind, monitor 190 and one or more aspects of the response array 200 is used to evaluate the positioning of a lead within a vein relative to a potential stimulation site on a target nerve. In one aspect, a repetitive stimulation pattern is applied from the stimulation module 192 of nerve integrity monitor 190 to the electrode portion 156 of lead 150 as the lead 150 is advanced distally during navigation of the ranine vein (or other vein). In some embodiments, the applied stimulation pattern is a 1 second burst of stimulation every 3 seconds, a ramping stimulation pattern, and/or a physician controlled burst. In another aspect, electromyography (EMG) monitoring electronics 196 of the nerve integrity monitor 190 enables measuring a muscle response to the nerve stimulation applied during navigation of the target veins. Accordingly, fine wire electrodes 308 (or similar) are connected in electrical communication with the nerve integrity monitor 190 and are used to continuously monitor the muscle activity in response to the stimulation patterns applied via electrode portion 156 during navigation of the lead 150. Using this arrangement, this closed loop feedback will allow the physician to obtain real-time feedback of a position (along the transvenous pathway) of the electrode leads 156 and feedback regarding the ability of the electrode leads 156 to capture the target nerve at a particular position of the electrode leads 156 along the transvenous pathway adjacent the target nerve. It is also understood that the methods described in association with FIGS. 1-3B for placement of lead 150 are applicable to placement of other leads described in association with FIGS. 4A-14.

Figure 5A:
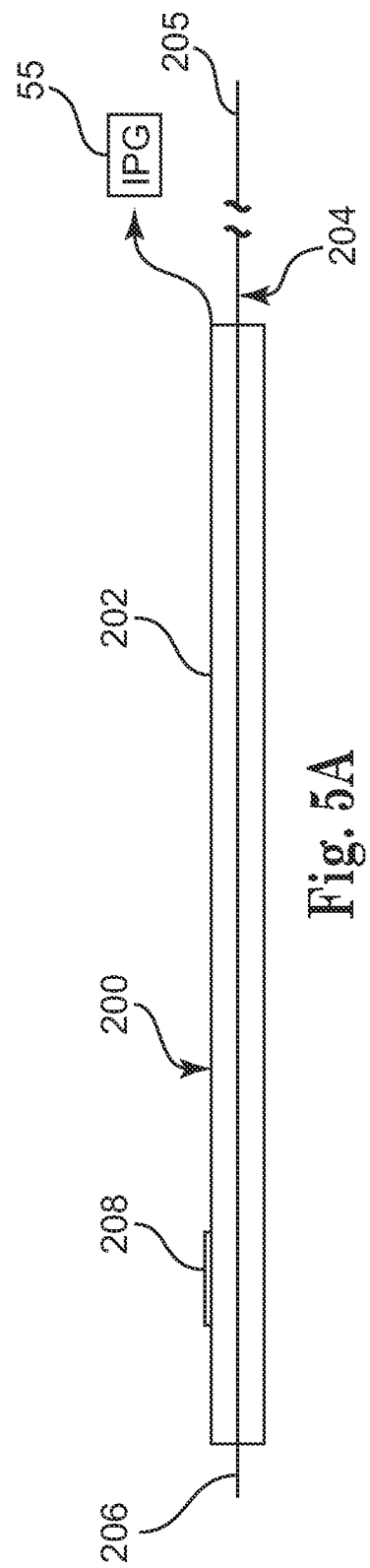
FIG. 5A is a side plan view of an over-the-wire delivery system for a stimulation lead, according to an embodiment of the present disclosure.
Figure 5B:
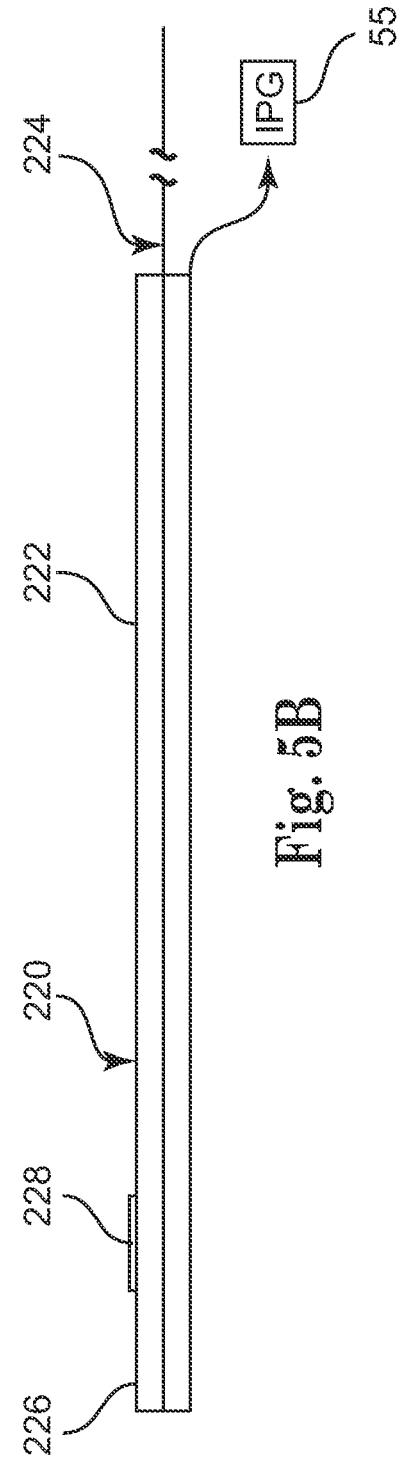
FIG. 5B is a side plan view of an stylet-driven delivery mechanism for a stimulation lead, according to an embodiment of the present disclosure.

In order to advance and deliver the electrode portion 156 of lead 150 to the target location, one embodiment of the present disclosure employs a delivery mechanism, such as one of the delivery mechanisms illustrated in FIGS. 5A-5B. In most instances, it is expected that the stimulation lead is introduced into a subclavian vein, however, other entry sites are not strictly excluded.

As illustrated in FIG. 5A, an over-the-wire lead system 200 includes an implantable lead 202 including at least one lumen (not shown) slidably advancable over a guide wire 204. In use, distal end 206 of steerable guide wire 204 is advanced through the vasculature 180 (FIG. 3A) to the target location and then lead 202 is advanced over the proximal portion 205 of guide wire 204 (and along the length of guide wire 204) until electrode portion 208 of lead 202 is located at the target stimulation site. In one aspect, lead 202 is in electrical communication with IPG 55 (FIG. 1) to enable IPG 55 to control operation of electrode portion 208 of lead 202. It is also understood that once electrode portion 208 is located optimally along a length of the vein (through which it extends), the lead 202 can be rotated to thereby rotate the electrode portion 208 to apply different stimulation effects to the various fascicles of the target nerve.

In another embodiment, a stylet-driven mechanism is employed to deliver electrode portion 156 of lead 150 to the target location to stimulate the hypoglossal nerve (or another target nerve). With this in mind, FIG. 5B illustrates a stylet lead system 220 that includes a lead 222 secured to a guide wire 224. In use, distal end 226 of steerable lead 222 is advanced through the vasculature 180 via advancing and steering guide wire 224 until electrode portion 228 of lead 222 is located at the target stimulation site. In one aspect, lead 202 is in electrical communication with IPG 55 (FIG. 1) to enable IPG 55 to control operation of electrode portion 228 of lead 220.

Referring again to FIG. 3A, in the one embodiment, lead 150 includes a lead body 152 that supports a respiratory sensor 154 (including first portion 155A and second portion 155B) at a proximal portion of lead body 152. In other words, the respiratory sensor 154 is provided on the same lead body 152 as the electrode portion 156 so that both the respiratory sensor 154 and the electrode portion 156 are placed in the vasculature 180 in a single pass. With this arrangement, as the electrode portion 156 is advanced distally for placement adjacent a target nerve, the respiratory sensor 154 becomes automatically placed within a pectoral region of the patient 20 to enable sensing the respiration pattern of the thorax of the patient. With this placement, the sensor 154 detects respiratory features and/or patterns (e.g., inspiration, expiration, respiratory pause, etc.) in order to trigger activation of electrode portion 156 to stimulate a target nerve. Accordingly, with this arrangement, the IPG 55 (FIG. 1) receives sensor waveforms from the respiratory sensor 154, thereby enabling the IPG 55 to deliver electrical stimulation synchronously with inspiration, such as with each respiratory breath (or another aspect of the respiratory pattern related to inspiration) according to a therapeutic treatment regimen in accordance with embodiments of the present disclosure. It is also understood that the respiratory sensor 154 is powered by the IPG 55 and the IPG 55 also contains internal circuitry to accept and process the impedance signal from the lead 150.

In some embodiments, a respiratory waveform is monitored and stimulation (generally synchronous with respiration) is not applied until a respiratory feature and/or pattern indicative of an apnea is identified. Stimulation is terminated upon detection that the apneic-indicative feature or pattern is no longer present within the monitored respiratory waveform.

In one embodiment, the respiratory sensor 154 is an impedance sensor. In one aspect, the impedance sensor is configured to sense a bio-impedance signal or pattern whereby the control unit evaluates respiratory patterns within the bio-impedance signal. For bio-impedance sensing, in one embodiment, electric current will be injected through electrode 155B and an electrically conductive portion of case 56 of the IPG 55 (FIG. 3A) and voltage will be sensed between electrode 155A and 155B (or also between 155A and the electrically conductive portion of case 56 of IPG 55) to compute the impedance.

In another embodiment of bio-impedance sensing, during the placement of the impedance sensing lead, the impedance waveform can be displayed on the programmer (108) in real time. The location of electrodes 155A and 155B can be interactively (an array of electrodes would be available to select from via a multiplexer switch within the IPG) adjusted to yield the optimal signal to noise ratio in represent the respiratory phase information.

In another embodiment, the sensor 154 is a pressure sensor. In one aspect, the pressure sensor in this embodiment detects pressure in the thorax of the patient. In another aspect, this pressure could be a combination of thoracic pressure and cardiac pressure (e.g., blood flow). With this configuration, the controller is configured to analyze this pressure sensing information to detect the respiratory patterns of the patient.

In some embodiments, lead 150 includes an anchor 158 that is locatable at a proximal portion of lead body 152. The anchor 158 is configured to ensure that sensor 154 and electrode portion 156 remain in the proper position within the vasculature 180.

Figure 6:
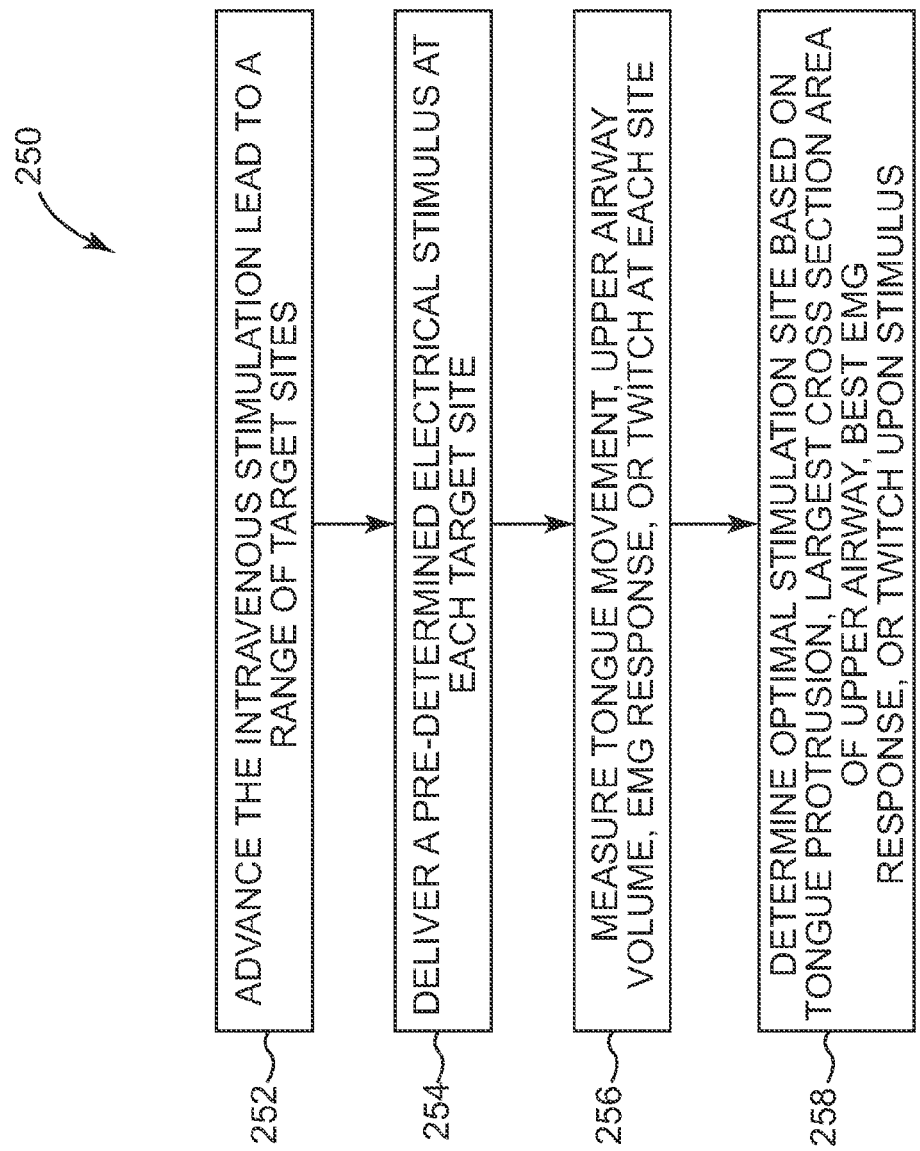
FIG. 6 is a schematic illustration of a method of selecting a stimulation site, according to an embodiment of the present disclosure.

The previously introduced FIGS. 1 and 3A generally depict a stimulation electrode portion 65,156 transvenously delivered into the ranine vein (i.e., the vena comitans of the hypoglossal nerve) to enable stimulating the hypoglossal nerve to treat sleep apnea. In one embodiment of the present disclosure, as illustrated in FIG. 6, a method 250 of treating apnea includes identifying an optimal site to locate stimulation electrode portion 156 (FIG. 3A) along a length of the ranine vein (or another vein suitable to apply stimulation to the hypoglossal nerve or another target nerve) that will result in a desired stimulation of the hypoglossal nerve. In particular, as illustrated in FIG. 6, in a first step 252 the lead 150 is advanced through the vasculature 180 (FIG. 3A) to a range of target sites within the ranine vein (or other nearby vein) and a pre-determined electrical stimulus is applied at each potential target site along the ranine vein (at 254). As illustrated at 256, upon the application of the electrical stimulus at each potential target site, the response to the stimulation is identified by: (1) a degree of tongue protrusion; (2) the size of cross-sectional area of the upper airway; (3) a best EMG response indicative of maintaining airway patency; and/or 4) a twitch from either the tongue or laryngeal muscle. As illustrated at 258, using the response data for each potential target site, the method 250 identifies one or more treatment sites (from among the potential target sites along the ranine vein) correlated with the greatest impact on maintaining airway patency during inspiration.

It is also understood that these steps 252-258 can be repeated iteratively, as necessary, until the optimal vein and the optimal stimulation location along that vein are identified. With this in mind, in employing method 250, one or more venous pathways might be explored before one or more veins (and a location along that vein(s)) are identified as being an optimal site(s) from which to apply an electrical stimulus. In other words, method 250 is not limited to evaluating target sites within a single vein adjacent a target nerve, but extends to evaluating several different veins adjacent to one or more target nerves. In this regard, method 250 is employed to identify the vein from among a group of veins that enables providing the most efficacious stimulus to a target nerve (e.g., nerves innervating the muscles of the upper airway including the genioglossal, hypoglossus, palatoglossus, etc.), and to identify the best location along one of the those sites to provide the most efficacious stimulus. As previously mentioned, in some embodiments, more than one vein is identified and used so that a stimulation signal is applied from two different veins toward the target nerve.

In one aspect, in evaluating multiple potential stimulation sites along a vein or along multiple veins, at each site the method 250 iteratively applies a stimulation signal with differing values for each signal parameter (e.g., polarity, pulse width, frequency, and amplitude) to determine which combination of values yields the best impact of the stimulation signal upon the target nerve at a potential site. In this way, each potential site is evaluated under conditions in which the stimulation signal would actually be applied were that potential site chosen as an optimal site for stimulation. In one embodiment, this determination of an optimal stimulation site via evaluating each of the stimulation parameters employs therapy module 106 in cooperation with stimulation module 104, a stimulation lead 150, and patient programming module 108, as previously described in association with FIGS. 1-3A.

Figure 7:
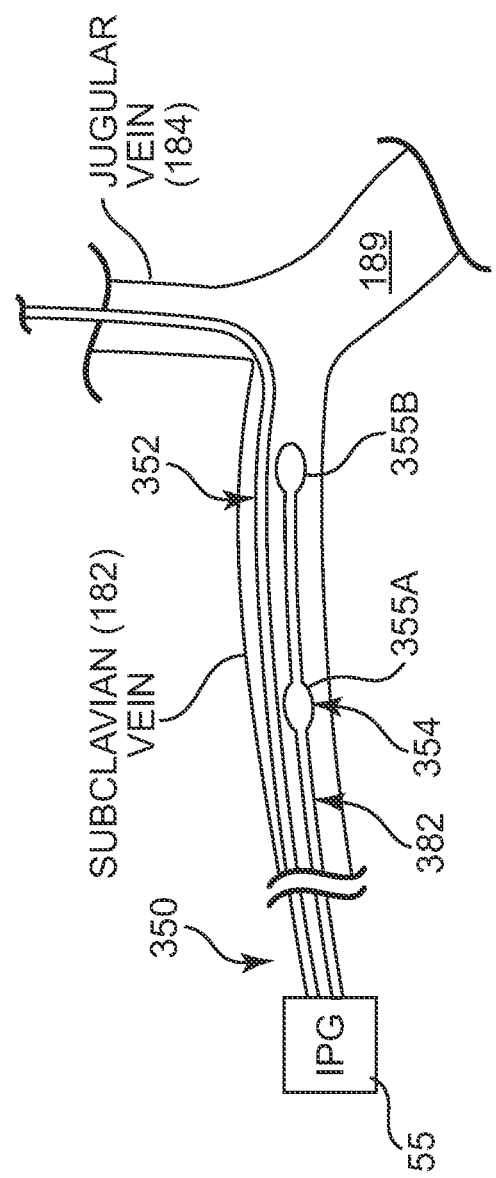
FIG. 7 is a schematic illustration of a transvenous placement of a stimulation lead and sensor for treating sleep apnea, according to an embodiment of the present disclosure.

FIG. 7 illustrates a stimulation lead system 350 to be deployed instead of lead 150, according to one embodiment of the present disclosure. Lead system 350 comprises substantially the same features and attributes as lead 150 (FIG. 3) except for providing the sensing portion along a separate lead body 382 from the lead body 352 that supports a stimulation electrode portion (not shown, but similar to electrode portion 156 in FIG. 3A). Accordingly, as illustrated in FIG. 7, lead system 350 includes a pair of lead bodies 352 and 382 with lead body 352 dedicated to supporting the stimulation electrodes and with lead body 382 dedicated to support the sensor 354. The lead body 382 supports sensor 354, including first portion 355A and second portion 355B spaced apart from each other along a length of lead body 382. In one embodiment, the lead body 382 has a length configured to orient both the first portion 355A and the second portion 355B within the subclavian vein 182. However, in other embodiments, the lead body has a length configured to orient one or both of the first portion 355A and the second portion 355B within one or more portions 189 of the vasculature 180 beyond the subclavian vein 182. In any case, sensor 354 is configured to monitor respiratory effort to detect patterns indicative of apneas/hypopneas, and to detect the patterns of inspiration, expiration, and/or respiratory pause, which may be used to trigger a therapeutic stimulation.

In some embodiments, sensor lead 382 of lead system 350 is not placed transvenously but is implanted subcutaneously, either adjacent to the pocket housing the IPG 55 or tunneled within tissue in the pectoral region surrounding the IPG 55. In other embodiments, sensor lead 382 additionally comprises a cardiac lead (epicardial or intra-cardiac) that is also used for a cardiac therapy (for example, therapies such as bradycardia, tachycardia, or heart failure).

While various different shapes and forms of leads can be used in the methods and systems of the present disclosure, FIGS. 8-14 illustrate several different exemplary embodiments of leads. In at least some of these embodiments, a fixation mechanism provides releasable fixation for a stimulation lead so that transvenous placement of a stimulation lead can be maintained for semi-permanent time period or can be reversed (i.e., removed) if necessary.

FIG. 8 is a side plan view schematically illustrating a lead 400 including a lead body 402 having a proximal portion 404 and a distal portion 406, which supports a stimulation electrode array 409. The electrode array 409 includes one or more surface electrodes 410 spaced apart along a length of the distal portion 406 of the lead body 402. In some embodiments, lead 400 includes an anchor 408 at the proximal portion 404 of lead body 402, which is configured to maintain the position of the lead body 402 relative to a length of the vein(s) through which the lead body 402 extends. In one aspect, this anchor 408 facilitates maintaining the position of the stimulation electrode array 409 at a desired site within the vein adjacent a desired stimulation site of the target nerve.

Once implanted, a transvenous stimulation system for automatically treating obstructive sleep apnea must remain stable and endure the normal activities of the patient. For example, the neck of a patient moves through a wide range of motion through many different positions. To counteract the potential for a stimulation lead to move back and forth within a vein (relative to a desired stimulation site), embodiments of the present disclosure provide an anchoring mechanism to anchor a distal portion of a stimulation lead within a vein at the desired stimulation site relative to a target nerve. These anchoring mechanisms insure that proper placement of the stimulation lead is maintained despite the dynamic motion and varying positions of the neck, which could otherwise cause inadvertent repositioning of the stimulation lead (relative to the target nerve) if the distal anchoring mechanisms were not present. Several embodiments of a distal anchoring mechanism are described and illustrated in association with FIGS. 9 and 11-14.

FIG. 9 is a side plan view schematically illustrating a lead 430 including a distal anchoring mechanism, in accordance with one embodiment of the present disclosure. In this embodiment, a lead 430 includes a lead body 432 having a proximal portion 434 and a distal portion 436, which supports a stimulation electrode array 439, as illustrated in FIG. 9. The electrode array 439 includes one or more surface electrodes 440 spaced apart along a length of the distal portion 436 of the lead body 432. In another aspect, distal portion 436 of lead body 432 comprises a distal anchoring mechanism arranged as a coiled configuration 450 and which is configured to maintain the position of the lead body 402 relative to a length of the vein(s) through which the lead body 402 extends. This coiled configuration acts to fix the distal portion 436 of the lead body 432 within the vein at the location at which the electrodes 440 will apply an electrical stimulus. In one aspect, prior to insertion of the lead 430 into the venous system, the distal portion 436 is in the coiled configuration 450. However, in order to install the lead 432 into the venous system, the distal portion 436 is converted from the coiled configuration 450 into a generally straight configuration (i.e., lacking coils) by advancing the guide wire through at least the distal portion 436 of the lead body 432. After maneuvering the guide wire and the lead 430 to the desired location within the venous system, the guide wire is removed proximally from the lead body 432, which allows the distal portion 436 to return to the coiled configuration 450. In one embodiment, this "memory effect" of the coiled configuration is achieved via incorporating materials such as Nitonal or thermo-formed polyurethane into the distal portion 436. In other embodiments, other materials having memory behavior, as known by those skilled in the art, are employed to form distal portion 436, thereby enabling the operation of coiled configuration 450.

In another aspect, as previously described in connection with method 250, each of the various stimulation parameters (for example, electrode polarity, amplitude, frequency, pulse width, and duration) are tested at each potential stimulation site as the stimulation lead 430 is maneuvered (through the venous system) adjacent to the target nerve. By evaluating the response at each location along the venous system (in the target nerve region) and noting the particular value or combination of stimulation parameters that yields the best response at that potential location, one can determine the optimal stimulation site for stimulation electrode array 439. As previously described herein, this method of determining a stimulation site (according to an effective group of corresponding values for the stimulation parameters) can be applied to anyone of the different stimulation electrode configurations within this present disclosure.

In another embodiment of the stimulation leads and as previously described in association with FIGS. 1-4B, two individual branches of the stimulation lead or two independent stimulation leads can be placed transvenously near both left and right side of the hypoglossal nerve. The IPG and programmer can control stimulation delivery to each branches of the stimulation lead either independently or dependently.

FIG. 10 is a perspective view illustrating another embodiment of the present disclosure. In this embodiment, a lead 500 includes an array of ring electrodes 502, 504, 506 at a distal portion of the lead 500 and which is configured to apply an electrical stimulus to a target nerve. In one aspect, this array of ring electrodes 502-506 is configured to direct an electrical field to a target nerve (e.g., hypoglossal nerve) spaced apart from the lead 500 within the vein (e.g., ranine vein). It is also understood that the ring electrodes 502-506 can be optionally employed in one or more of the other embodiments described in association with FIGS. 8-9 and 11-14.

FIG. 11 is a perspective view schematically illustrating a lead 520 including a distal anchoring mechanism, in accordance with one embodiment of the present disclosure. In this embodiment, the lead 520 includes a stent portion 522 at a distal portion of the lead 520, and in which the stent portion 522 includes one or more stimulation electrodes 524, 526, 528 incorporated into (or added onto) the structure (e.g., struts) of the stent. In one aspect, this array of electrodes 524-528 supported by the stent structure 522 is configured to direct an electrical field to a target nerve (e.g., hypoglossal nerve) spaced apart from the lead 500 within the vein (e.g., ranine vein). Moreover, the stent structure 522 provides a mechanism to secure the location of the electrodes 524-528 at a desired placement along a length of the vein (through which the lead 520 extends) corresponding to a desired stimulation site of a target nerve.

In one embodiment, the stent structure 522 is arranged in a collapsed state (having a diameter generally represented by A in FIG. 11) during insertion into the venous system and the vein adjacent the target nerve. Once the stent structure 522 and associated stimulation electrodes are located a potential stimulation site, the physician initiates conversion of the stent structure 522 from its collapsed state to an expanded state (having a diameter generally represented by B in FIG. 11) to contact the walls of the vein, which in turn, anchors the electrodes in place. In other words, the stent structure 522 acts as a distal fixation mechanism that fixates the distal portion of the lead within the vein at the desired stimulation site. In one aspect, during the process of evaluating different potential stimulation sites, the stent structure is temporarily expanded to test the effectiveness of a stimulation signal at a potential stimulation site and then re-collapsed to enable repositioning the lead 520 along the vein to place the electrodes and stent structure at a different potential stimulation site. This process is repeated as many times as necessary until the optimal stimulation site is determined, where the stent structure 522 is then re-expanded to secure and maintain the distal portion of the lead 520 at the optimal stimulation site. It is understood that the selective expansion, collapse, and final fixation of the stent structure in an expanded state is performed according to techniques known in the art, such as manipulating the stent structure 522 via rotation, pushing, and/or pulling of a guide wire.

In other embodiments, instead of using the coiled configuration 350 of FIG. 9 or the stent structure of FIG. 11, fixation of a distal portion of a stimulation lead within a vein is achieved via other mechanisms.

Figure 12A:
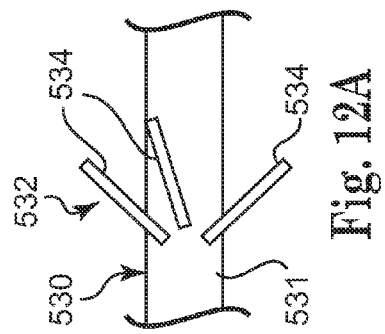
FIG. 12A is a side plan view of a distal portion of a stimulation lead including an array of selectively deployable tines shown in a deployed configuration, according to an embodiment of the present disclosure.
Figure 12B:
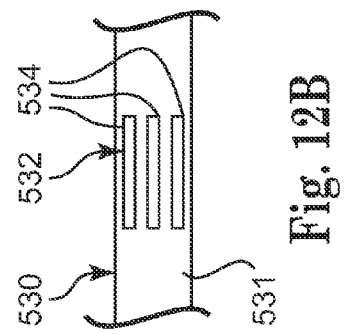
FIG. 12B is a side plan view of the lead of FIG. 12A with the tines shown in a storage position, according to an embodiment of the present disclosure.

FIGS. 12A-12B schematically illustrate a transvenous stimulation lead 530 including a distal fixation mechanism, according to one embodiment of the present disclosure. As illustrated in FIG. 12A, a distal portion 531 of the stimulation lead 530 includes a distal fixation mechanism provided via an array 532 of deployable tines 534. In FIG. 12A, tines 534 are shown in a deployed configuration in which tines 534 extend radially from the body of distal portion 531 of lead 530. In this position, the tines 534 are configured to releasably engage the walls of a vein to thereby anchor the distal portion 531 within the vein. It is understood that the tines are configured in a manner as to not negatively impact the integrity of the walls of the vein.

In one aspect, as the distal portion of the lead is advanced through the venous system, a guidewire is used to position these tines 534 into a storage position generally against an outer wall of the lead, as schematically illustrated in FIG. 12B. After a suitable stimulation site has been determined, the tines 534 are deployed (i.e., selectively expanded radially outward away from the outer wall of the lead as shown in FIG. 12A) to engage the walls of the vein to thereby anchor the distal portion 531 of the lead at the desired stimulation site along that vein (and adjacent to the desired location along the target nerve). In some embodiments, the deployable tines 534 are made of a polyurethane material and/or a Nitonal spring.

It is understood that the array 532 of tines 534 is located on distal portion 531 of lead 530 at a position sufficiently close to an electrode stimulation portion of lead 530 (such as one of the electrode configurations illustrated throughout this application) to insure that the electrode stimulation portion is generally fixed within a vein at a location corresponding to a desired stimulation site of a target nerve.

Figure 13A:
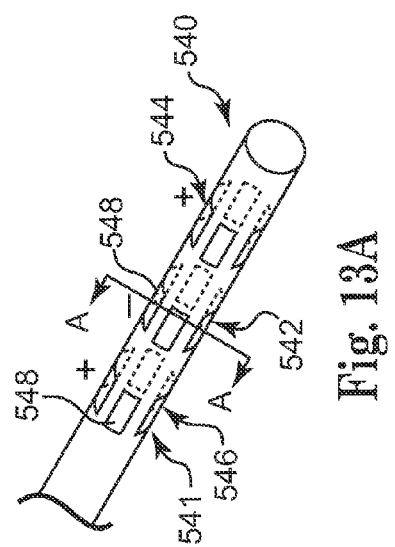
FIG. 13 is a perspective view of a distal portion of a stimulation lead including a programmable array of electrodes mounted circumferentially around the lead, according to an embodiment of the present disclosure.
Figure 13B:
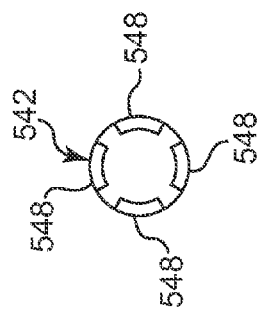

FIG. 13 is a perspective view illustrating a transvenous stimulation lead 540 configured to apply an electrical stimulus to a target nerve, according to another embodiment of the present disclosure. In this embodiment, the lead 540 includes a series 541 of programmable arrays 542, 544, 546 of electrode portions 548 with the respective arrays 542, 544, 546 spaced apart from each other along a length of the distal portion of the lead 540. In one aspect, the respective electrode portions 548 of each array extend circumferentially about an outer surface of lead 540 in a spaced apart relationship to form a general ring-shaped configuration. In one aspect, the programmable arrays 542-546 of electrode portions 548 are configured to direct an electrical field from a location within the vein (e.g., ranine vein) to a target nerve (e.g., hypoglossal nerve) spaced apart from the lead 540. It is also understood that the arrays 542-546 of electrodes can be optionally employed in one or more of the other embodiments described in association with FIGS. 8-9 and 11-12B.

In one embodiment, each array 542, 544, 546 of electrodes comprises two, three, four or more independent electrode portions 548. In one aspect, the electrode portions 548 are independently programmed to stimulation the target stimulation site. In other words, at any given time, a stimulation signal is applied from zero, one, two, or more electrode portions 548 of each separate array 542-546. In this embodiment, the many varied positions of the electrode portions both along the length of the distal portion of the lead 540 and circumferentially or radially about the lead 540 enables precise activation of selective groups of electrode portions 548 (at their various spaced apart locations) to produce a stimulation signal at virtually any point relative to the distal portion of lead 540. Accordingly, this arrangement enables stimulation of a target nerve (or select portions/fascicles of a target nerve) with little or no rotation of the lead 540 to direct the stimulation to the target stimulation site.

Figure 14:
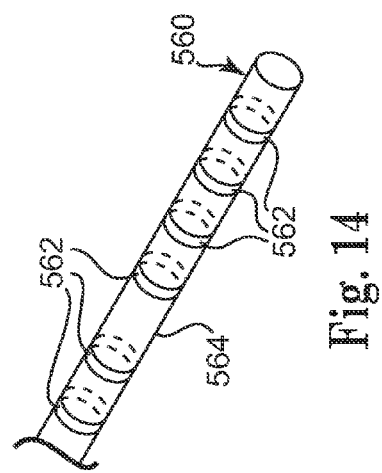
FIG. 14 is a perspective view of a distal portion of a stimulation lead including an array of programmable ring electrodes, according to an embodiment of the present disclosure.

FIG. 14 is a perspective view illustrating a transvenous stimulation lead 560 configured to apply an electrical stimulus to a target nerve, according to another embodiment of the present disclosure. In this embodiment, a lead 560 includes a programmable array of ring electrodes 562 mounted at a distal portion 564 of the lead 560. In one aspect, this programmable array of ring electrodes 562 is configured to direct an electrical field from the location of the respective ring electrodes 562 within the vein (e.g., ranine vein) to a target nerve (e.g., hypoglossal nerve) spaced apart from the lead 560. It is also understood that the ring electrodes 562 can be optionally employed in one or more of the other embodiments described in association with FIGS. 8-9 and 11-12B. In one embodiment, each ring 562 may be independently programmed to stimulate the target stimulation site. In this embodiment, the many varied positions of the ring electrodes 562 along the length of the distal portion of the lead 560 enables precise activation one, two, or more ring electrodes 562 (at their various spaced apart locations) to produce a stimulation signal at virtually any point along a length of the distal portion of lead 560. Accordingly, this arrangement enables stimulation of a target nerve with little or no rotation of the lead 560 to direct the stimulation to the target stimulation site. Moreover, once lead 560 is located generally in the region of interest, the lead 560 need not be maneuvered extensively distally or proximally within the vein in order to position an electrode adjacent to a desired stimulation site of a nerve because any one or combination of the ring electrodes 562 along the length of the distal portion of the lead are available for activation to apply a stimulation signal to the target nerve. In one embodiment, the array of electrodes 562 has a length that substantially matches a majority of a length of the hypoglossal nerve, as it extends from a position near the jugular vein toward the genioglossus muscle. In one aspect, this length of the array enables determining which electrodes 562 of the array produce the most efficacious respiratory airway patency without having to reposition the array within the vasculature. In another aspect, an efficacious respiratory airway patency is determined upon identifying which ring electrode 562 or combination of ring electrodes 562 produces a longest duration of increased airway patency, a largest size of increased airway patency, and/or a substantial reduction in apneas.

In this embodiment, the lead does not require rotation of the lead to direct the stimulation to the target stimulation site. Further with multiple rings attached the control unit, minimal positioning of the lead within the vein is required as optimal stimulation settings may be evaluated using multiple combinations of active or inactive electrode rings.

Several different embodiments have been described in association with FIGS. 1-7, in which an IPG 55 is implanted in a pectoral region and in which a sensor electrode(s) and a stimulation electrode(s) (extending from the IPG 55) are delivered transvenously to sense respiratory patterns and to apply a stimulation signal, respectively. In addition, several embodiments of stimulation electrode arrays (and associated distal fixation mechanisms) have been described in association with FIGS. 8-14. Moreover, it is understood that in some embodiments, a lead is transvenously placed in each side of the body (left and right) such that bilateral (simultaneous or alternating) stimulation takes place on the left and/or right hypoglossal nerve (or other target nerve). With these various embodiments in mind, it is further understood that among those embodiments, several configurations are provided in which at least two electrodes are spaced apart in the body in the vicinity of the upper airway such that an impedance is measurable between the two spaced apart electrodes to provide an indication of airway patency (e.g., opening and/or closing of the upper airway). For example, to measure this impedance, one of the stimulations electrodes is placed transvenously on a first side of the body and the other one of the stimulation electrodes is placed transvenously on a second side of the body. In some embodiments, this bio-impedance is measured as a trans-thoracic bio-impedance, a trans-laryngeal bio-impedance, or a trans-pharyngeal bio-impedance.

In some configurations, the spaced electrodes are both stimulation electrodes, while in other configurations, the spaced apart electrodes comprise one stimulation electrode and one respiratory sensor electrode. In yet other configurations, the two spaced apart electrodes (used for measuring an impedance indicative of airway patency) include one of the electrodes comprising at least one of a stimulation electrode and a respiratory sensor electrode and the other one of the electrodes comprising an electrode formed by an electrically conductive portion of a case 56 or housing of the IPG 55.

Moreover, in some embodiments, the respective electrodes portions provide a dual function in that each electrode provides a respiratory sensing function or a stimulation function as well as acting as a part of a pair of impedance sensing electrodes. On the other hand, in other embodiments, at least one electrode of the pair of impedance sensing electrodes does not also act to sense respiration (e.g. inspiration) or to stimulate but rather is dedicated for use in sensing impedance to detect or indicate a degree of airway patency.

Accordingly, by using a pair of electrodes to sense an impedance that is indicative of airway patency, a system operating according principles of the present disclosure enables detection of apnea event by indicating whether or not a collapse of the airway has taken place. In one embodiment, this impedance-based indication of airway patency is used along with other physiologic sensing information (such as the sensing information described at least in association with FIGS. 2A-2B) to detect an apnea event, and to potentially trigger stimulation of a target nerve to restore airway patency in accordance with the embodiments of the present disclosure.

FIG. 15A is a side plan view schematically illustrating a nerve stimulation system 600 for treating obstructive sleep apnea, according to an embodiment of the present disclosure. In this embodiment, as illustrated in FIG. 15A, system 600 provides therapy to a patient 602 reclined on a support 604 (e.g. a bed) and a headrest structure 606 (e.g., pillow), which houses a power source/controller 622 and one or more radiofrequency transmission coils 620. However, it is understood that this embodiment is not strictly limited to a bed 604 and/or pillow, but extends to other furniture configurations in which the patient 602 can remain stationary for an extended period of time. As further illustrated in FIG. 15A, system 600 includes a microstimulator 635 which is delivered transvenously into the ranine vein 188 (or other nearby vein) for stimulating the hypoglossal nerve 190 (or other target nerve), as illustrated in FIG. 15B. In some embodiments, transvenous delivery of microstimulator 635 is accomplished via techniques substantially similar to those previously described in association with FIGS. 9, 11, 12A-12B, as well as via transvenous delivery methods to be further described in association with FIGS. 16-17C.

In one embodiment, microstimulator 635 comprises a generally elongate member including circuitry for generating a neurostimulation signal and at least one electrode 637 arranged on a surface of the micro stimulator 635 for transmitting the signal to nerve 190, as illustrated in FIG. 15B. In some embodiments, microstimulator 635 comprises a microminiature electronic device such as that described in Richmond et al. U.S. Pat. No. 6,240,316, and which is hereby incorporated by reference in its entirety. However, it is understood that in the context of the present disclosure, such micro stimulators are delivered transvenously instead of being directly implanted into a target muscle.

In general terms, system 600 applies a treatment regimen for treating obstructive sleep apnea according to sensing methods and stimulation parameters at least substantially the same as those previously described in association with FIGS. 1-14, including the potential use of bilateral stimulation (for simultaneous or alternate stimulation from the left and right sides of the body) via the use of two separate microstimulators.

Referring again to FIG. 15A, system 600 includes at least one sensing component configured to provide respiratory sensing suitable for detection of an apnea and for triggering application of the stimulation signal synchronous with respiration, such as with inspiration. In some embodiments, respiratory sensing is provided via an externally securable belt 630 including a respiratory pressure sensor 631. Signals sensed at sensor 631 are transmitted wirelessly to power/controller 622 for use in apnea detection and treatment. In other embodiments, respiratory sensing is provided via an impedance sensor 640 which is secured on an external surface of a chest via a patch or even implanted subcutaneously. Sensor 640 communicates wirelessly with power/controller 622. In some embodiments, belt 630 or the other sensor 640 includes an accelerometer or piezoelectric transducer for detecting body motion/position, with such information also being used by controller 622 and/or microstimulator 635 to determine when to monitor for apneas and/or when to treat apneas.

In use, as the patient reclines on the support 604, respiratory sensor 631 or 640 provides information about respiratory effort which is monitored via a power/controller 622. Once a treatment threshold is detected, power/controller 622 generates power which is communicated to micro stimulator 635 via radiofrequency/transmission coils 620. It is also understood that in some embodiments, microstimulator 635 stores programmed instructions for applying a stimulation signal according to an obstructive sleep apnea treatment regimen, while in other embodiments micro stimulator 635 receives such programmed instructions from controller 622 via coils 620. In either case, the instructions are also programmable by a clinician or by a patient (within certain physician-authorized constraints). With this in mind, the microstimulator 635, in turn, selectively stimulates nerve 190 (FIG. 15B) according to a treatment regimen to restore airway patency, thereby alleviating the obstructive sleep apnea.

In some embodiments, as illustrated in FIG. 15C, respiratory sensing information is obtained via sensors arranged on a garment 675 configured to be worn by the patient 602 during a time period when apneas might potentially occur (e.g. sleeping, resting). In one embodiment, garment 675 provides a respiration sensing belt 682 similar to belt 630, while in other embodiments garment 675 comprises one or more impedance sensors or other respiratory effort sensors 684 (and/or body motion/position detectors) on a pectoral region 680 of the garment 675.

Figure 16:
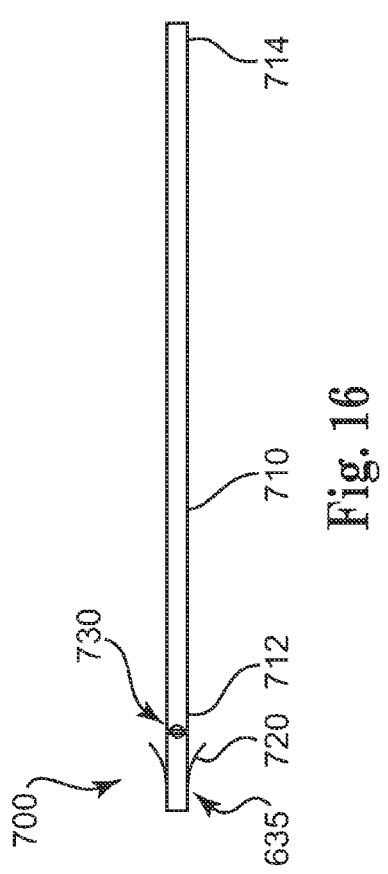
FIG. 16 is a side plan view schematically illustrating an anchoring system of a transvenously delivered microstimulator, according to an embodiment of the present disclosure.

FIG. 16 is a side plan view schematically illustrating an anchoring system of a transvenously delivered microstimulator, according to an embodiment of the present disclosure. Accordingly, in some embodiments, as illustrated in FIG. 16, a transvenous delivery mechanism 700 includes a steerable catheter/stylet 710 including a proximal portion 714 and a distal portion 712. The micro stimulator 635 is releasably secured at distal portion 712 of steerable catheter/stylet 710 via release mechanism 730. Using techniques known to those skilled in the art, catheter 710 is used to advance and maneuver the microstimulator 635 transvenously until adjacent to a desired stimulation site of a target nerve. At this location, the release mechanism 730 is activated to secure micro stimulator 635 within the vein adjacent the target nerve and the remainder the catheter 710 is then withdrawn from the vein leaving the microstimulator 635 within the vein. While various mechanisms can be used to secure the microstimulator 635 within the vein, in this embodiment, an array of selectively deployable tines 720 (or other selectively deployable anchors) extends radially outward from micro stimulator 635 to secure the microstimulator 635 relative to the vein and, thereby relative to the target nerve.

Figure 17B:
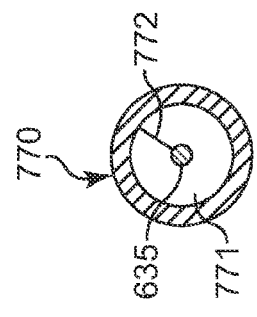
FIG. 17B is a sectional view schematically illustrating a microstimulator and a stent of the anchoring system of FIG. 17A, according to an embodiment of the present disclosure.
Figure 17C:
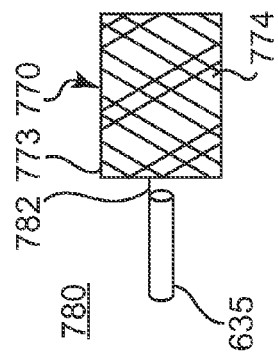
FIG. 17C is a side plan view schematically illustrating a microstimulator and a stent of the anchoring system of FIG. 17A, according to an embodiment of the present disclosure.
Figure 17A:
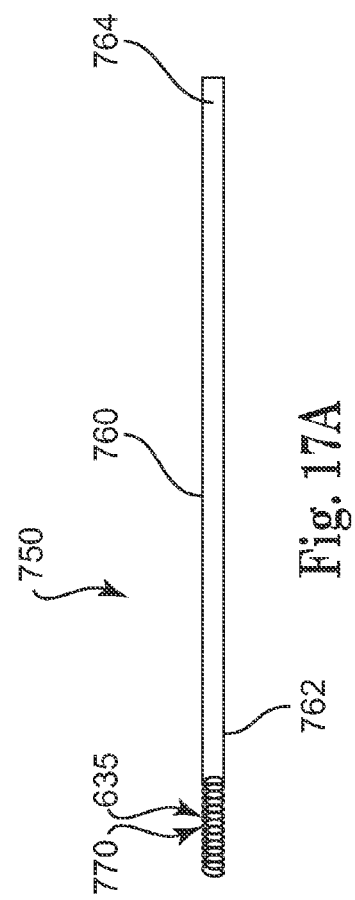
FIG. 17A is a side plan view schematically illustrating a stent-based anchoring system of a transvenously delivered microstimulator, according to an embodiment of the present disclosure.

FIG. 17A is a side plan view schematically illustrating a stent-based anchoring system of a transvenously delivered microstimulator configured to treat obstructive sleep apnea, according to an embodiment of the present disclosure. In this embodiment, a microstimulator 635 is coupled to a stent 770. A steerable catheter/stylet 760 is adapted to transvenously deliver (using techniques known to those skilled in the art) the combination of the stent 770 (in its collapsed state) and the microstimulator 635 to a location within a vein adjacent a target nerve. Further manipulation of the steerable catheter 760 results in release and expansion of the stent 770 to be secured relative to the walls of the vein and then withdrawal of the catheter/stylet 760. With this arrangement, the microstimulator 635 becomes generally fixed relative to a length of the vein and therefore generally fixed relative to a portion of the target nerve.

In some embodiments, micro stimulator 635 is coupled to extend within an interior 771 of stent 770, as illustrated in FIG. 17B. In one embodiment, micro stimulator 635 is coupled relative to the stent 770 via one or more semi-rigid or resilient tethers 772.

In yet other embodiments, microstimulator 635 is configured to extend distally forward from (or proximally relative to) an end 773 of stent 770 via support 782 (which extends from one or more struts 774), as illustrated in FIG. 17C. accordingly, in this arrangement, microstimulator 635 is not located within the interior 771 (FIG. 17B) of stent 770, which may lessen any potential interference of the body of stent 770 relative to the stimulation signal from microstimulator 635.

Embodiments of the transvenously-delivered microstimulator (described herein) enable precise location of a microstimulator adjacent to an optimal neurostimulation site because the transvenous approach enables the surgeon to vary the position of the microstimulator along the length of a vein (using the steerable catheter techniques) and thereby vary the position of the microstimulator along the length of the target nerve. This method allows the surgeon to identify a precise optimal stimulation site that causes contraction of one or more specific muscles (suited to restore airway patency) prior to fixing the location of the micro stimulator relative to the target nerve. Moreover, steerable catheter/stylets or other transvenous delivery instruments enable rotation of the microstimulator within the vein to further adjust the effect of the stimulation on a target nerve or portions of the target nerve.

Embodiments of the present disclosure provide an implantable system to provide therapeutic solutions for patients diagnosed with obstructive sleep apnea. The system is designed to stimulate the hypoglossal nerve during inspiration thereby preventing occlusions in the upper airway during sleep.

While at least one exemplary embodiment has been presented in the foregoing detailed description, it should be appreciated that variations exist. It should also be appreciated that the exemplary embodiment or exemplary embodiments are only examples, and are not intended to limit the scope, applicability, or configuration of the present disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the present disclosure as set forth in the appended claims and the legal equivalents thereof.

The invention claimed is:

1. A method of treating sleep apnea, comprising:
    implanting an implantable pulse generator subcutaneously at a pectoral, non-vasculature location within a body of a patient and connecting a single lead to the pulse generator, wherein the single lead includes a stimulation electrode portion that is in electrical communication with the pulse generator, with the stimulation electrode portion being separate from, and independent of, stimulation circuitry of the pulse generator;
    inserting the single lead within a non-cardiac vasculature of the body and advancing the single lead through the non-cardiac vasculature; and
    positioning the stimulation electrode portion of the single lead within the non-cardiac vasculature in close proximity to the hypoglossal nerve to apply a nerve-stimulation signal, wherein positioning the stimulation electrode portion comprises:
    arranging the stimulation electrode portion on a distal portion of the single lead and arranging a respiratory sensing portion on a proximal portion of the single lead; and
    distally advancing the single lead within the non-cardiac vasculature to simultaneously cause:
        positioning the stimulation electrode portion within a first vein of the non-cardiac vasculature in close proximity to the hypoglossal nerve and within a neck region of the patient; and
        positioning the respiratory sensing portion within a second vein of the non-cardiac vasculature within a pectoral region of the patient, the second vein in fluid communication with the first vein.

2. The method of claim 1, wherein applying the nerve-stimulation signal comprises:
    synchronizing the application of the nerve-stimulation signal with respiration.

3. The method of claim 2, wherein synchronizing the application comprises:
    applying the nerve-stimulation signal to occur at each respiratory breath.

4. The method of claim 2, comprising:
    sensing at least one respiratory feature via positioning a second respiration sensor on an exterior surface of a patient's body; and
    wireles sly coupling the second respiration sensor to the implantable pulse generator.

5. The method of claim 4, wherein sensing the at least one respiratory feature comprises:
    measuring a trans-thoracic bio-impedance to track the relative amplitude of the respiratory waveform.

6. The method of claim 4, wherein sensing the at least one respiratory feature includes additionally measuring at least one of:
    a body motion parameter;
    an electrocardiography parameter; and
    a blood oxygen parameter.

7. The method of claim 1, comprising:
    wherein sensing, via the respiratory sensing portion, the at least one respiratory feature to track the relative amplitude of the respiratory waveform, and
    determining an average peak amplitude based on the tracked relative amplitudes; and
    detecting, via the at least one respiratory feature, an apneic respiration pattern as cyclic variations of an amplitude of the trans-thoracic bio-impedance relative to the average peak amplitude for a duration corresponding to a nominal apneic duration.

8. The method of claim 1, wherein applying the nerve-stimulation signal comprises:
    detecting an apneic-indicative respiratory pattern prior to applying the nerve-stimulation signal;
    synchronizing the application of the nerve-stimulation signal with respiration; and
    discontinuing application of the nerve-stimulation signal when the apneic-indicative respiratory pattern is no longer detected.

9. The method of claim 1, comprising:
arranging the stimulation portion to include an array of independently programmable electrode elements spaced apart from each other along a length of the stimulation portion and spaced apart from each other circumferentially on the outer surface of the stimulation portion; and
identifying at least one target site along a length of the hypoglossal nerve via applying a stimulation signal to different combinations of the electrode elements and evaluating which combination of electrode elements achieves an efficacious respiratory airway patency.

10. The method of claim 1, comprising:
arranging the stimulation portion to include an array of electrodes spaced apart from each other along a length of the stimulation portion; and
identifying at least one target site along a length of the hypoglossal nerve via applying a stimulation signal separately to each electrode or electrode combination, on a one-at-a-time basis, and evaluating which electrode or electrode combination achieves an efficacious respiratory airway patency.

11. The method of claim 10, comprising:
arranging a length of the array to substantially match a majority of a length of the hypoglossal nerve extending from a position near the jugular vein toward the genioglossus muscle; and
determining which electrodes of the array produce the efficacious respiratory airway patency without repositioning the stimulation portion within the non-cardiac vasculature after the stimulation is first positioned in close proximity to the hypoglossal nerve.

12. The method of claim 10, wherein identifying the at least one target portion comprises determining the most efficacious response for each potential target site via at least one of:
determining a degree of tongue motor response;
determining an increased cross-sectional area of an upper respiratory airway;
determining a degree of electromyography response of one or more tongue-protrusion related muscles;
detecting a twitch from either the tongue or laryngeal muscle; or
detecting a reduction in apnea events.

13. The method of claim 10, comprising:
determining, at each potential target site of the hypoglossal nerve, a therapeutic neurostimulation signal via applying a test neurostimulation signal while iteratively varying a value for each signal parameter of a plurality of signal parameters, wherein the signal parameters include at least one of an amplitude, a pulse width, an electrode polarity, a duration, and/or a frequency.

14. The method of claim 1, wherein the first vein comprises a ranine vein and the second vein comprises a subclavian vein.

15. The method of claim 1, comprising:
arranging the respiratory sensing portion as a first sensing element and a second sensing element spaced apart from the first sensing element along a length of the single lead.

16. The method of claim 15, comprising:
performing sensing a trans-thoracic bio-impedance relating to respiratory patterns via measuring a voltage across the first sensing element relative to the second sensing element.

17. The method of claim 1, wherein positioning the stimulation portion comprises:
providing the stimulation portion as at least part of an anchoring mechanism;
advancing the stimulation portion within the non-cardiac vasculature, with the anchoring mechanism in a generally collapsed state, to a first test stimulation site along the hypoglossal nerve;
manipulating the anchoring mechanism into an expanded state to engage a side wall of the non-cardiac vasculature at the first test stimulation site and applying a first neurostimulation test signal, via the stimulation portion, to the hypoglossal nerve;
manipulating the anchoring mechanism into the generally collapsed state to disengage the anchoring mechanism from the side wall of the non-cardiac vasculature and advancing the stimulation portion to a second test stimulation site spaced apart along the length of the hypoglossal nerve from the first test stimulation site; and
manipulating the anchoring mechanism into the expanded state to re-engage the side wall of the non-cardiac vasculature and applying a second neurostimulation test signal, via the stimulation portion, the hypoglossal nerve.

18. The method of claim 17, comprising providing the anchor mechanism at a distal portion of the single lead as a stent structure including a generally tubular member, wherein the collapsed state corresponds to a first diameter of the stent structure and the expanded state corresponds to a second diameter substantially larger than the first diameter and sized to engage the side wall of the non-cardiac vasculature.

19. The method of claim 1, wherein the implantable pulse generator includes a power supply and the stimulation electrode portion is powered via the single lead by the implantable pulse generator.

20. The method of claim 1, wherein the portion of the single lead extending between the implantable pulse generator and the stimulation electrode portion and which provides electrical communication between the implantable pulse generator and the stimulation electrode portion is without stimulation circuitry.

21. The method of claim 1, comprising:
sensing at least one respiratory feature via delivering a second respiration sensor subcutaneously within a patient's body external to the non-cardiac vasculature.

22. The method of claim 21, wherein sensing the at least one respiratory feature includes additionally measuring at least one of:
a respiratory flow parameter; and
a time-of-day parameter.

23. The method of claim 21, comprising:
arranging the second respiration sensor to include at least an accelerometer; and
using measurements from the accelerometer in association with application of the nerve-stimulation signal.

24. A method of treating sleep apnea, comprising:
implanting an implantable pulse generator subcutaneously at a pectoral, non-vasculature location within a body of a patient and connecting a single lead to the pulse generator, wherein a distal portion of the single lead includes a stimulation electrode portion that is in electrical communication with the pulse generator, with the stimulation electrode portion being separate from, and independent of, stimulation circuitry of the pulse generator;

inserting the single lead within a non-cardiac vasculature of the body and advancing the single lead through the non-cardiac vasculature;

positioning the stimulation electrode portion of the single lead within a first vein of the non-cardiac vasculature in a neck region of a patient in close proximity to the hypoglossal nerve to apply a nerve-stimulation signal; and arranging at least a first portion of a respiratory sensing portion on a second portion of the single lead proximal to, and spaced apart from, the stimulation electrode portion to position the first portion of the respiratory sensing portion within a second vein of the non-cardiac vasculature within the pectoral region of the patient, wherein the second vein is in fluid communication with the first vein.

25. The method of claim 24, comprising:
arranging at least a second portion of the respiratory sensing portion to be implanted within the body in a location external to the non-cardiac vasculature.

26. The method of claim 24, comprising:
arranging at least a second portion of the respiratory sensing portion to be worn externally on the patient's body.

27. The method of claim 25, wherein arranging the second portion of the respiratory sensing portion to be at least part of the implanted pulse generator, and comprising:
arranging the second portion to include at least an electrically conductive portion of a case of the implantable pulse generator, and wherein the method further comprises:
determining respiratory information based on a bio-impedance measurable between the respective first and second portions of the respiratory sensing portion.

28. The method of claim 25, comprising:
arranging the second portion of the respiratory sensing portion to include at least an accelerometer; and
using measurements from the accelerometer in association with application of the nerve-stimulation signal.

29. The method of claim 28, wherein the accelerometer is configured to measure a body activity parameter at least partially indicative of sleep apnea behavior.

30. The method of claim 23, wherein the accelerometer is configured to measure a body activity parameter at least partially indicative of sleep apnea behavior.

* * * * *